US009574007B2

(12) United States Patent
Mather et al.

(10) Patent No.: US 9,574,007 B2
(45) Date of Patent: *Feb. 21, 2017

(54) B7-H3L CELL SURFACE ANTIGEN AND ANTIBODIES THAT BIND THERETO

(71) Applicant: MacroGenics, Inc., Rockville, MD (US)

(72) Inventors: Jennie P. Mather, Millbrae, CA (US); Ronghao Li, Millbrae, CA (US); Zhuangyu Pan, Millbrae, CA (US); Penelope E. Roberts, Millbrae, CA (US)

(73) Assignee: MacroGenics, Inc., Rockville, MD (US)

( * ) Notice: Subject to any disclaimer, the term of this patent is extended or adjusted under 35 U.S.C. 154(b) by 82 days.

This patent is subject to a terminal disclaimer.

(21) Appl. No.: 14/294,935

(22) Filed: Jun. 3, 2014

(65) Prior Publication Data

US 2014/0328857 A1    Nov. 6, 2014

Related U.S. Application Data

(60) Division of application No. 12/413,483, filed on Mar. 27, 2009, now Pat. No. 8,779,098, which is a continuation of application No. 10/600,802, filed on Jun. 19, 2003, now Pat. No. 7,527,969.

(60) Provisional application No. 60/390,203, filed on Jun. 19, 2002.

(51) Int. Cl.

| A61K 39/395 | (2006.01) |
| C07K 16/30 | (2006.01) |
| C07K 14/705 | (2006.01) |
| C07K 16/28 | (2006.01) |
| G01N 33/574 | (2006.01) |
| A61K 45/06 | (2006.01) |
| A61K 47/48 | (2006.01) |
| A61N 5/10 | (2006.01) |
| A61K 38/00 | (2006.01) |
| A61K 39/00 | (2006.01) |

(52) U.S. Cl.
CPC ......... *C07K 16/30* (2013.01); *A61K 39/39558* (2013.01); *A61K 45/06* (2013.01); *A61K 47/48569* (2013.01); *A61N 5/10* (2013.01); *C07K 14/70532* (2013.01); *C07K 16/2827* (2013.01); *G01N 33/57492* (2013.01); *A61K 38/00* (2013.01); *A61K 2039/505* (2013.01); *C07K 2317/77* (2013.01); *G01N 2333/70503* (2013.01)

(58) Field of Classification Search
None
See application file for complete search history.

(56) References Cited

U.S. PATENT DOCUMENTS

| 4,676,980 A | 6/1987 | Segal et al. |
| 4,816,567 A | 3/1989 | Cabilly et al. |
| 5,552,391 A | 9/1996 | Coutts et al. |
| 5,565,332 A | 10/1996 | Hoogenboom et al. |
| 5,580,717 A | 12/1996 | Dower et al. |
| 5,656,444 A | 8/1997 | Webb et al. |
| 5,733,743 A | 3/1998 | Johnson et al. |
| 5,807,715 A | 9/1998 | Morrison et al. |
| 5,866,692 A | 2/1999 | Shitara et al. |
| 5,997,867 A | 12/1999 | Waldmann et al. |
| 6,001,359 A | 12/1999 | Bright et al. |
| 6,054,297 A | 4/2000 | Carter et al. |
| 6,054,561 A | 4/2000 | Ring |
| 6,180,377 B1 | 1/2001 | Morgan et al. |
| 6,265,150 B1 | 7/2001 | Terstappen et al. |
| 6,331,415 B1 | 12/2001 | Cabilly et al. |
| 6,416,999 B1 | 7/2002 | Li et al. |
| 6,429,303 B1 | 8/2002 | Green et al. |
| 6,436,704 B1 | 8/2002 | Roberts et al. |
| 6,441,163 B1 | 8/2002 | Chari et al. |
| 6,891,030 B2 | 5/2005 | Chen |
| 6,965,018 B2 | 11/2005 | Mikesell et al. |
| 7,279,567 B2 | 10/2007 | Mikesell et al. |
| 2003/0039999 A1 | 2/2003 | Yoshinaga et al. |
| 2003/0134283 A1 | 7/2003 | Peterson et al. |
| 2003/0162186 A1 | 8/2003 | Bejanin et al. |
| 2004/0077043 A1 | 4/2004 | Watarai et al. |
| 2004/0162236 A1 | 8/2004 | Alsobrook, II et al. |
| 2004/0236088 A1 | 11/2004 | Heuer et al. |
| 2005/0202536 A1 | 9/2005 | Chen |
| 2006/0154313 A1 | 7/2006 | Anderson et al. |
| 2006/0275287 A1 | 12/2006 | St Croix et al. |
| 2007/0292885 A1 | 12/2007 | Bejanin et al. |

FOREIGN PATENT DOCUMENTS

| EP | 0519596 | 12/1992 |
| EP | 1292619 | 3/2003 |
| EP | 1327638 | 7/2003 |
| EP | 1514933 | 3/2005 |
| EP | 1892251 | 2/2008 |
| WO | WO 99/46281 | 9/1999 |
| WO | WO 00/68266 | 11/2000 |
| WO | WO 01/14557 | 3/2001 |
| WO | WO 01/18021 | 3/2001 |
| WO | WO 01/18204 | 3/2001 |

(Continued)

OTHER PUBLICATIONS

Abrams, J.R. et al. (1999) "*CTLA4Ig-Mediated Blockade of T-Cell Costimulation in Patients With Psoriasis Vulgaris*," J. Clin Invest. 103(9):1243-1252.

(Continued)

*Primary Examiner* — Laura B Goddard
*Assistant Examiner* — Meera Natarajan
(74) *Attorney, Agent, or Firm* — William C. Schrot; AuerbachSchrot LLC

(57) ABSTRACT

The invention provides the identification and characterization of disease and cancer-associated antigen, RAAG10. The invention also provides a family of monoclonal antibodies that bind to antigen RAAG10, methods of diagnosing and treating various human cancers and diseases that express RAAG10.

16 Claims, 2 Drawing Sheets

(56) References Cited

FOREIGN PATENT DOCUMENTS

| WO | WO 01/77303 | 10/2001 |
|---|---|---|
| WO | WO 01/89567 | 11/2001 |
| WO | WO 01/94413 | 12/2001 |
| WO | WO 02/08279 | 1/2002 |
| WO | WO 02/10187 | 2/2002 |
| WO | WO 02/32375 | 4/2002 |
| WO | WO 02/099119 | 12/2002 |
| WO | WO 03/068938 | 8/2003 |
| WO | WO 04/001381 | 12/2003 |

OTHER PUBLICATIONS

Agarwal, A. et al. (2008) "The role of positive costimulatory molecules in transplantation and tolerance," Curr. Opin. Organ Transplant. 13:366-372.
Albino, A.P. et al. (1983) "Biochemical Analysis of a 130,000 Molecular Weight Glycoprotein on Human Melanoma Cells," J. Immunol. 131(3):1595-1599.
Anonymous, (2000) "New Products for Molecular Biotechnology," Molec. Biol. 16:293-294.
Arrufo, A. and Seed, B. (1987). "Molecular Cloning of a CD28 cDNA by a High Efficiency COS Cell Expression System," Proc. Natl. Acad. Sci. U.S.A. 84:8573-8577.
Banki et al. (1994) "Cloning and Expression of the Human Gene for Transaldolase," J. Biol. Chem. 269(4)2847-2851.
Bendayan et al. (1995) "Possibilities of False Immunochemical Results Generated by the Use of Monoclonal Antibodies: The Example of the Anti-proinsulin Antibody," J. Histochem. Cytochem. 43(9):881-886.
Bernard, A. et al. (2005) "T and B Cell Cooperation: A Dance of Life and Death," Transplantation 79:S8-S11.
Bertram, E.M. (2004) "Role of T Cell Costimulation in Anti-Viral Immunity," Seminars in Immunol. 16:185-196.
Blazar, B.R. et al. (1999) "*Opposing Roles of CD28:B7 and CTLA-4:B7 Pathways in Regulating In Vivo Alloresponses in Murine Recipients of MHC Disparate T Cells*," J. Immunol. 162(11):6368-6377.
Bodey et al. (2000) "Failure of Cancer Vaccines: The Significanct Limitations of this Approach to Immunotherapy," Anticancer Res. 20:2665-2676.
Boon (1992) "Toward an Genetic Analysis of Tumor Rejection Antigens," Adv. Canc. Res. 58:177-210.
Brown, B.A. et al. (1987). "Tumor-Specific Genetically Engineered MurinelHuman Chimeric Monoclonal Antibody," Cancer Res. 47:3577-3583.
Brunet, J.F. et al. (1987) "*A New Member of the Immunoglobulin Superfamily—CTLA-4*," Nature 328(6127):267-270.
Carter et al., "Humanization of an anti-p185HER2 antibody for human cancer therapy," Proc. Natl. Acad. Sci. USA 89:4285-4289, 1992.
Castriconi, R. et al. (2004) "*Identification of 4Ig-B7-H3 As a Neuroblastoma-Associated Molecule That Exerts a Protective Role From an NK Cell-Mediated Lysis*," Proc. Natl. Acad. Sci. (U.S.A.) 101(34):12640-5. Epub Aug. 16, 2004.
Chapoval, A.I. et al. (2001) "B7-H3: A Costimulatory Molecule for T Cell Activation and IFN-Gamma Production," Nature Immunology. 2 (2001). 269-274.
Chen, S. et al. (2000) "Surface Antigen Expression and Complement Susectibility of Differentiated Neuroblastoma Clones,"Amer. J. Pathol. 156(3):1085-1091.
Clauser, K.R. et al. (1999). "Role of Accurllte Mass Measurement (± 10 ppm) in Protein Identification Strategies Employing MS or MSIMS and Database Searching," Analytical Chemistry 71(4):2871-2882.
Co, M.S. et al. (1992). "Chimeric and Humanized Antibodies with Specificity for the CD33 Antigen," J. Immunol.148(4): 1149-1154.
Co, M.S. et al. (1991). "Humanized Antibodies for Antiviral Therapy," Proc. Natl Acad Sci. US.A. 88:2869-2873.

Collins, M. et al. (2005) "The B7 Family of Immune-Regulatory Ligands," Genome Biol. 6:223.1-223.7.
Coyle, A.J. et al. (2001) "The Expanding B7 Superfamily: Increasing Complexity in Costimulatory Signals Regulating T Cell Function," Nature Immunol 2(3):203-209.
Crispen, P.L. et al. (2008) "*Tumor Cell and Tumor Vasculature Expression of B7-H3 Predict Survival in Clear Cell Renal Cell Carcinoma*," Clin Cancer Res. 14(16):5150-5157 Epub Aug. 11, 2008.
Daugherty, B.L. et al. (1991). Polymerase:Chain Reaction Facilitates the Cloning, CDR-Grafting, and Rapid Expression ofa Murine Monoclonal Antibody Directed Against the CD18 Component of Leukocyte Integrins, II Nucl. Acids Res. 19(9):2471-2476.
Dermer (1994) "Another Anniversary fo the War on Cancer," Bio/Technology 12:320.
Dillman, R.O. et al. (1988). "Superiority of an Acid-Labile Daunorubicin-Monoclonal Antibody Immunoconjugate Comarec,i to Free Drug," Cancer Res. 48:6097-6102.
Dong, C. et al. (2003) "Immune Regulation by Novel Costimulatory Molecules," Immunolog. Res. 28(1):39-48.
Dong, H. et al. (1999) "*B7-H1, A Third Member of the B7 Family, Co-Stimulates T-Cell Proliferation and Interleukin-10 Secretion*," Nat Med. 5(12):1365-1369.
Emamaullee, J. et al. (2009) "*Costimulatory Blockade With Belatacept in Clinical and Experimental Transplantation—A Review*," Expert Opin Biol Ther. 9(6):789-796.
Flies, D.B. et al. (2007) "The New B7s: Playing a Pivotal Role in Tumor Immunity," J. Immunother. 30(3):251-260.
Gennaro, A.R. ed. (2000). Remington: The Science and Practice of Pharmacy; Twentieth Edition, Lippincott Williams & Wilkins: Philadelphia, PA pp. xiv-xv (Table of Contents Only).
Gharandaghi, F. et al. (1999)."Mass Spectrometric Identification of Proteins From Silver-Stained Polyacrylamide Gel: A Method for the Removal of Silver Ions to Enhance Sensitivity," Electrophoresis 20:601-605.
Goldenberg, D.M. ed. (1995). Cancer Therapy With Radiolabeled Antibodies CRC Press: Boca Raton, FL, four pages (Table of Contents Only).
Gorman, S.D. et al. (1991). "Reshaping a Therapeutic CD4 Antibody," Proc. Natl. Acad. Sci. U.S.A. 88:4181-4185.
Greenwald, R.J. et al. (2005) "The B7 Family Revisited," Ann. Rev. Immunol 23:515-548.
Hashiguchi, M. et al. (2008) "*Triggering Receptor Expressed on Myeloid Cell-Like Transcript 2 (TLT-2) Is a Counter-Receptor for B7-H3 and Enhances T Cell Responses*," Proc. Natl. Acad. Sci. (U.S.A.) 105(30):10495-10500.
Henry, J. et al. (1999) "*Structure and Evolution of the Extended B7 Family*," Immunol Today. 20(6):285-288.
Hofmeyer, K. et al. (2008) "The Contrasting Role of B7-H3," Proc. Natl. Acad. Sci. (U.S.A.) 105(30):10277-10278.
International Search report for PCT/US03/19819 (May 19, 2005) (5 pages).
Jones, P.T. et at. (1986). "Replacing the Complementarity-Determining Regions in a Human Antibody With Those From a Mouse," Nature 321 :522-525.
Kettleborough, C.A. et al. (1991). "Humanization of a Mouse Monoclonal Antibody by CDR Grafting: The Importance of Framework Residues on Loop Conformation," Protein Engineering 4:(7)773-783.
Khawli, L.A. et al. (2008) "Cytokine, Chemokine, and Co-Stimulatory Fusion Proteins for the Immunotherapy of Solid Tumors," Exper. Pharmacol. 181:291-328.
Kirk, A.D. et al. (1997) "*CTLA4-Ig and Anti-CD40 Ligand Prevent Renal Allograft Rejection in Primates*," Proc. Natl. Acad. Sci. (U.S.A.) 94(16):8789-8794.
Kirkin et al. "Melanoma-Associated Antigens Recognized by Cytotoxic T Lymphocytes," (1998) APMIS 106:665-679.
Kohler, G. and Milstein, C. (1975). "Continuous Cultures of Fused Cells Secreting Antibody of Predefined Specificity," Nature 256:495-497.
Korman, A.J. et al. (2007) "Checkpoint Blockade in Cancer Immunotherapy," Adv. Immunol. 90:297-339.

(56) References Cited

OTHER PUBLICATIONS

Kristiansen, O.P. et al. (2000) "*CTLA-4 in Autoimmune Diseases—A General Susceptibility Gene to Autoimmunity?*" Genes Immun. 1(3):170-184.

Larsen, C.P. et al. (1996) "*Long-Term Acceptance of Skin and Cardiac Allografts After Blocking CD40 and CD28 Pathways*," Nature 381(6581):434-438.

Leach, D.R. et al. (1996) "*Enhancement of Antitumor Immunity by CTLA-4 Blockade*," Science. 271(5256):1734-1736.

Lee et al. (1999) "*Increased Vaccine-Specific T Cell Frequency After Peptide-Based Vaccination Correlates with Increased Susceptibility to In Vitro Stimulation But Does Not Lead to Tumor Regression*" J. Immunol. 163:6269-6300.

Linsley, P.S. et al. (2009) "The Clinical Utility of Inhibiting CD28-Mediated Co-Stimulation," Immunolog. Rev. 229:307-321.

LoBuglio, A.F. et al. (1989). "Mouse/Human Chimeric Monoclonal Antibody in Man: Kinetics and Immune Response," *Proc. Natl. Acad. Sci. U.S.A.* 86:4220-4224.

Loke, P. et al. (2004) "Emerging Mechanisms of Immune Regulation: The Extended B7 Family and Regulatory T Cells." Arthritis Res. Ther. 6:208-214.

Lonberg, N. and Huszar, D. (1995). "Human Antibodies From Transgenic Mice," *Int. Rev. Immunol.* 13:65-93.

Maeda, H. et al. (1991). "Construction of Reshaped Human Antibodies with UN-Neutralizing Activity," *Human Antibodies Hybridoma* 2:124-134.

Mahato, R.I. et al. (1991). "Cationic Lipid-Based Gene Delivery Systems: Pharmaceutical Perspectives," *Pharm. Res.* 14(7):853-859.

Mahnke, K. et al. (2007) "*Induction of Immunosuppressive Functions of Dendritic Cells In Vivo by CD4+CD25+ Regulatory T Cells: Role of B7-H3 Expression and Antigen Presentation*." Eur J Immunol. Aug. 2007;37(8):2117-26.

Mangham, D.C. and Isaacson, P.G. (1999). "A Novel Immunohistochemical Detection System Using Mirror Image Complementary Antibodies (MICA)," *Histopathology* 35(2): 129-133.

Martin-Orozco, N. et al. (2007) "Inhibitory Costimulation and Anti-Tumor Immunity," Semin. Cancer Biol. 17(4):288-298.

Modak, S. et al. (1998) "*Novel Tumor-Associated Surface Antigen: Broad Distribution Among Neuroectodermal, Mesenchymal and Epithelial Tumors, With Restricted Distribution in Normal Tissues*," Program/Proceedings, American Society of Clinical Oncology, 34th Annual Meeting, May 16-19, 1998, p. 445a; Abstract 1716.

Modak, S. et al. (2001) "*Monoclonal Antibody 8H9 Targets a Novel Cell Surface Antigen Expressed by a Wide Spectrum of Human Solid Tumors*," Cancer Res. 61(10):4048-4054.

Modak, S. et al. (Mar. 1999) "*Disialoganglioside GD2 and Antigen 8H9: Potential Targets for Antibody-Based Immunotherapy Against Desmoplastic Small Round Cell Tumor (DSRCT) and Rhabdomyosarcoma (RMS)*," Proceedings of the American Association for Cancer Research Annual Meeting, vol. 40:474 (90th Annual Meeting of the American Association for Cancer Research; Philadelphia, Pennsylvania, US; Apr. 10-14, 1999.

Modak, S. et al. (Mar. 2000) "*Radioimmunotargeting to Human Rhabdomyosarcoma Using Monoclonal Antibody 8H9*," Proc. Am. Assoc. Cancer Res.41:724.

Paul, William E, (1993) "Fundamental Microbiology, 3 Ed." p. 242-243.

Peeters, K. et al. (2001). "Production of Antibodies and Antibody Fragments in Plants," *Vaccine* 19:2756-2761.

Pollock, D.P. et al. (1999). "Transgenic Milk as a Method for the Production of Recombinant Antibodies," *J. Immunol. Methods* 231:147-157.

Prasad, D.V. et al. (2004) "*Murine B7-H3 Is a Negative Regulator of T Cells*," J. Immunol. 173:2500-2506.

Riechrnann, L. et al. (1988). "Reshaping Human Antibodies for Therapy," *Nature* 332:323-327.

Sato, K. et al. (1993). "Reshaping a Human Antibody to Inhibit the Interleukin 6-Dependent Tumor Cell Growth," *Cancer Res.* 53:851-856.

Sharpe, A.H. et al. (2002) "The B7-CD28 Superfamily," Nature Rev. Immunol. 2.116-126.

Shaw, D.R. et al. (1987). "Characterization of a MouselHuman Chimeric Monoclonal Antibody (17-IA) to a Colon Cancer Tumor-Associated Antigen," *J. Immunol.* 138(12):4534-4538.

Shen, W-C. and Ryser, H. J-P. (1981). "CIS-Aconityl Spacer Between Daunomycin and Macromolecular Carriers: A Model of ph-Sensitive Linkage Releasing Drug from a Lysosomotropic Conjugate," *Biochem. Biophys. Res. Commun.* 102(3):1048-1054.

Smith, R.T. (1994) "Cancer and the Immune System," Clin. Immunol. 41(4):841-849.

Steinberger, P. et al. (2004) "*Molecular Characterization of Human 4Ig-B7-H3, a Member of the B7 Family With Four Ig-Like Domains*," Am Assoc Immunol, 172(4):2352-9.

Stephan, J-P. et al. (1999). "Distribution and Function of the Adhesion Molecule BEN During Rat Development," *Dev. Biol.* 212:264-277.

Stephan, J-P. et al. (1999). "Selective Cloning of Cell Surface Proteins Involved in Organ Development: Epithelial Glycoprotein Is Involved in Normal Epithelial Differentiation," *Endocrinology*. 140(12): 5841-5854.

Subudhi, S.K. et al. (2005) "The Balance of Immune Responses: Costimulation Verse Coinhibition," J. Mol. Med. 83:193-202.

Suh, W.K. et al. (2003) "*The B7 Family Member B7-H3 Preferentially Down-Regulates T Helper Type 1-Mediated Immune Responses*," Nat Immunol. 4(9):899-906. Epub Aug. 17, 2003.

Sun, M. et al. (2000). "Characterization of Mouse and Human B7-H3 Genes," *J Immunol.* 168: 6294-6297.

Sun, M. et al. (2002) "*Characterization of Mouse and Human B7-H3 Genes*," J. Immunol. 168:6294-6297.

Supplemental Partial European Search Report (Mar. 12, 2007) for EP 03761281.9 (5 pages).

Tempest, P.R. et at. (1991). "Reshaping a Human Monoclonal Antibody to Inhibit Human Respiratory Syncytial Virus Infection in Vivo," *Bio/Technoiogy* 9:266-271.

Tivol, E.A. et al. (1995) "*Loss of CTLA-4 Leads to Massive Lymphoproliferation and Fatal Multiorgan Tissue Destruction, Revealing a Critical Negative Regulatory Role of CTLA-4* ," Immunity 3(5):541-547.

Tran, C.N. et al. (2008) "*Interactions of T Cells With Fibroblast-Like Synoviocytes: Role of the B7 Family Costimulatory Ligand B7-H3* ," J Immunol, 180(5):2989-2998.

Trouet, A. et al. (1982). "A Covalent Linkage Between Daunorubicin and Proteins that is Stable in Serum and Reversible by Lysosomal Hydrolases, As Required for a Lysosomotropic Drug-Carrier Conjugate: In vitro and in vivo Studies," *Proc. Natl. Acad. Sci. USA*. 79:626-629.

Vandenborre, K. et al. (1999) "*Interaction of CTLA-4 (CD152) With CD80 or CD86 Inhibits Human T-Cell Activation*," Immunology 98(3):413-421.

Verhoeyen, M. et al. (1988). "Reshaping Human Antibodies: Grafting an Antilysozyme Activity," *Science* 239:1534-1536.

Viglietta, V. et al. (2007) "Modulating Co-Stimulation," Neurotherapeutics 4:666-675.

Wang, S. et al. (2004) "Co-Signaling Molecules of the B7-CD28 Family in Positive and Negative Regulation of T Lymphocyte Responses," Microbes Infect. 6:759-766.

Weiner, L.M. et al. (2001). "Therapeutic Monoclonal Antibodies: General Principles," Section 5, Chapter 20; In Cancer: Principles and Practice of Oncology Sixth Edition Lippincott Williams & Wilkins: Philadelphia, PA, pp. 495-508.

Wheatley, S.P. and Wang, Y -L. (1998). "Indirect Immunofluorescence Microscopy in Cultured Cells," Chapter 18 in Methods in Cell Biology Mather, J.P. and Barnes, D. eds. Academic Press vol. 57, pp. 313-332.

White et al. (2001) "Antibody-Targeted Immunotherapy for Treatment of Malignancy," Ann. Rev. Med. 52:125-145.

Winter, G. and Milstein, C. (1991). "Man-Made Antibodies," *Nature* 349:293-299.

(56) References Cited

OTHER PUBLICATIONS

Winter, G. et al. (1994). "Making Antibodies by Phage Display Technology," *Annu. Rev. Immunol.* 12:433-455.
Woodruff, T.K. (1998). "Cellular Localization ofmRNA and Protein: In Situ Hybridization Histochemistry and in Situ Ligand Binding," Chapter 19 in Methods in Cell Biology Mather, J.P. and Barnes, D. eds. Academic Press vol. 57, pp. 333-351.
Xu, H. et al. (2006) "*Soluble Mouse B7-H3 Down-Regulates Dendritic Cell Stimulatory Capacity to Allogenic T Cell Proliferation and Production of IL-2 and IFN-Gamma*," Cell Mol Immunol. 3(3):235-240.
Xu, H. et al. (2009) "*MicroRNA miR-29 Modulates Expression of Immunoinhibitory Molecule B7-H3: Potential Implications for Immune Based Therapy of Human Solid Tumors*," Cancer Res. 69(15):5275-6281.
Yang, H.M. and Reisfeld, R.A. (1988). "Pharmacokinetics and Mechanism of Action of a Doxorubicon-Monoclonal Antibody 9.2.27 Conjugate Directed to a Human Melanoma Proteoglycan," *J. Natl. Canc. Inst.* 80:1154-1159.
Yi. K.H. et al. (2009) "Fine Tuning the Immune Response Through B7-H3 and B7-H4," Immunol. Rev. 229:145-151.
Zang, X. et al. (2007) "*B7-H3 and B7x Are Highly Expressed in Human Prostate Cancer and Associated With Disease Spread and Poor Outcome*," Proc. Natl. Acad. Sci. (U.S.A.) 104(49):19458-19463 Epub Nov. 27, 2007.
Zang, X. et al. (2007) "*The B7 Family and Cancer Therapy: Costimulation and Coinhibition*," Clin. Cancer Res. 13:5271-5279.
Zips et al. (2005) "*New Anti-Cancer Agents: In Vitro and In Vivo Evaluation*," In Vivo 19:1-8.
Kyriakos et al. (1992) "*The Fate of Antibodies Bound to the Surface of Tumor Cells in Vitro*," Cancer Res., 52: 835-842.
Bowie et al. (1990) "*Deciphering the Message in Protein Sequences: Tolerance to Amino Acid Substitutions*," Science 247:1306-1310.
Lenschow et al. (1996) "*CD28/B7 System of T Cell Costimulation*," Annu. Rev. Immunol. 14:233-58.
Rogers et al. (1988) "*Several Epitopes of p85 Glycoprotein (CDw44) are Dependent on Intact Disulphide Bonds, Isolation of cDNA Clones Requires a Polyclonal Antibody Raised Against the Reduced Protein*," Bioscience Reports 8(4):359-368.

B7-H3L CELL SURFACE ANTIGEN AND ANTIBODIES THAT BIND THERETO

CROSS-REFERENCE TO RELATED APPLICATIONS

This application is a divisional of U.S. application Ser. No. 12/413,483, filed Mar. 27, 2009, which application is a continuation of U.S. application Ser. No. 10/600,802, filed Jun. 19, 2003, now U.S. Pat. No. 7,527,969, which applications claim the benefit of U.S. provisional application Ser. No. 60/390,203, filed Jun. 19, 2002, which applications are incorporated herein by reference in their entireties and to which priority is claimed.

TECHNICAL FIELD

This invention is in the fields of biology and immunotherapy. More specifically, it concerns a novel disease and cancer-associated antigen, RAAG10, and a family of monoclonal antibodies that bind to RAAG10. The invention further provides the diagnosis and/or treatment of a variety of human diseases and cancers associated with RAAG10 using anti-RAAG10 family antibodies.

BACKGROUND OF THE INVENTION

In addition to their known uses in diagnostics, antibodies have been shown to be useful as therapeutic agents. For example, immunotherapy, or the use of antibodies for therapeutic purposes has been used in recent years to treat cancer. Passive immunotherapy involves the use of monoclonal antibodies in cancer treatments. See for example, *Cancer: Principles and Practice o/Oncology*, 6<sup>th</sup> Edition (2001) Chapt. 20 pp. 495-508. These antibodies can have inherent therapeutic biological activity both by direct inhibition of tumor cell growth or survival and by their ability to recruit the natural cell killing activity of the body's immune system. These agents can be administered alone or in conjunction with radiation or chemotherapeutic agents. Rituximab and Trastuzumab, approved for treatment of non-Hodgkin's lymphoma and breast cancer, respectively, are two examples of such therapeutics. Alternatively, antibodies can be used to make antibody conjugates where the antibody is linked to a toxic agent and directs that agent to the tumor by specifically binding to the tumor. Gemtuzumab ozogamicin is an example of an approved antibody conjugate used for the treatment of leukemia. Monoclonal antibodies that bind to cancer cells and have potential uses for diagnosis and therapy have been disclosed in publications. See, for example, the following patent applications which disclose, inter alia, some molecular weights of target proteins: U.S. Pat. No. 6,054,561 (200 kD c-erbB-2 (Her2), and other unknown antigens 40-200 KD in size) and U.S. Pat. No. 5,656,444 (50 kD and 55 kD, oncofetal protein). Example of antibodies in clinical trials and/or approved for treatment of solid tumors include: Trastuzumab (antigen: 180 kD, HER2/neu). Edrecolomab (antigen: 40-50 kD. Ep-CAM), Anti-human milk fat globules (HMFG1) (antigen >200 kD. HMW Mucin), Cetuximab (antigens: 150 kD and 170 kD, EGF receptor), Alemtuzumab (antigen: 21-28 kD, CD52), and Rituximab (antigen: 35 kD, CD20).

The antigen targets of trastuzumab (Her-2 receptor), which is used to treat breast cancer, and cetuximab (EGF receptor), which is in clinical trials for the treatment of several cancers, are present at some detectable level on a large number of normal human adult tissues including skin, colon, lung, ovary, liver, and pancreas. The margin of safety in using these therapeutics is possibly provided by the difference in the level of expression or in access of or activity of the antibody at these sites.

Another type of immunotherapy is active immunotherapy, or vaccination, with an antigen present on a specific cancer(s) or a DNA construct that directs the expression of the antigen, which then evokes the immune response in the individual, i.e., to induce the individual to actively produce antibodies against their own cancer. Active immunization has not been used as often as passive immunotherapy or immunotoxins.

Several models of disease (including cancer) progression have been suggested. Theories range from causation by a single infective/transforming event to the evolution of an increasingly "disease-like" or 'cancer-like' tissue type leading ultimately to one with fully pathogenic or malignant capability. Some argue that with cancer, for example, a single mutational event is sufficient to cause malignancy, while others argue that subsequent alterations are also necessary. Some others have suggested that increasing mutational load and tumor grade are necessary for both initiation as well as progression of neoplasia via a continuum of mutation-selection events at the cellular level. Some cancer targets are found only in tumor tissues, while others are present in normal tissues and are up-regulated and/or over-expressed in tumor tissues. In such situations, some researchers have suggested that the over-expression is linked to the acquisition of malignancy, while others suggest that the over-expression is merely a marker of a trend along a path to an increasing disease state.

What is needed are novel targets on the surface of diseased and/or cancer cells that may be used to treat such diseases and/or cancers with antibodies and other agents which specifically recognize the cell surface targets. There exists a further need, based on the discoveries disclosed herein, for novel antibodies and other agents which specifically recognize targets on the surface of cells that can modulate, either by reducing or enhancing, the disease-promoting activities of RAAG10.

As will be described in more detail below, the present inventors have discovered a novel antigen, which we refer to herein as RAAG10 and sometimes as B7-H3L, identified as the antigen target of the novel antibodies provided herein. Similar polypeptides are known. See, for example, Sun et al., J. Immunol. 2002, 168:6294-6297 which describes the identification of a mouse B7-H3 homolog, and characterizes the human B7-H3 gene as being shown to mediate T cell proliferation and IFN-gamma production.

SUMMARY OF THE INVENTION

The invention provides for monoclonal antibodies that bind to RAAG10, which is expressed on a variety of human cancers. In one aspect, the invention is a family of monoclonal antibodies that bind to RAAG10.

In another aspect, the invention is a monoclonal antibody anti-RAAG10 that is produced by any one of the host cell lines deposited on Apr. 9, 2002 and Apr. 23, 2002 at the American Type Culture Collection, having an address of 10801 University Boulevard, Manassas, Va., 20110-2209, and accorded Patent Deposit Designations of PTA-4217, PTA-4218, PTA-4244, and PTA-4245.

In yet another aspect, the invention is a method of generating monoclonal antibody anti-RAAG10 reactive with diseased and/or cancerous cells comprising the steps of: (a) immunizing a host mammal with an immunogen: (b)

obtaining lymphocytes from the mammal; (c) fusing lymphocytes (b) with a myeloma cell line to produce a hybridoma; (d) culturing the hybridoma of (c) to produce monoclonal antibodies; and (e) screening the antibodies to select only those antibodies which bind to diseased and/or cancerous cells or cell lines but do not bind to non-cancerous or normal cells or cell lines, or bind to normal cells at a lower level or in a different fashion.

In another aspect, the invention is a method of generating an anti-RAAG10 family antibody comprising culturing a host cell encoding such antibody or progeny thereof under conditions that allow production of the antibody, and purifying the anti-RAAG10 antibody.

In another aspect, the invention provides methods of generating any of the antibodies (or polypeptides) described herein by expressing one or more polynucleotides encoding the antibody (which may be separately expressed as a single light or heavy chain, or both a light and a heavy chain are expressed from one vector) in a suitable cell, generally followed by recovering and/or isolating the antibody or polypeptides of interest.

In another aspect, the invention is an anti-RAAG10 antibody or a polypeptide (which may or may not be an antibody) that competitively inhibits preferential binding of an anti-RAAG10 antibody to RAAG10. In some embodiments, the invention is an antibody or a polypeptide (which may or may not be an antibody) that binds preferentially to the same or different epitopes on RAAG10 as other anti-RAAG10 antibodies.

In yet another aspect, the invention is a composition comprising RAAG10 bound by an antibody specific for an epitope of RAAG10. In one embodiment, the antibody is anti-RAAG10. In other embodiments, two or more anti-RAAG10 antibodies are administered, with such antibodies mapping to two or more different epitopes of RAAG10. In some embodiments, the anti-RAAG10 antibody is linked to a therapeutic agent or a detectable label.

In another aspect, the invention is an antibody comprising a fragment or a region of an anti-RAAG10 antibody. In one embodiment, the fragment is a light chain of the antibody. In another embodiment, the fragment is a heavy chain of the antibody. In yet another embodiment, the fragment contains one or more variable regions from a light chain and/or a heavy chain of the antibody. In yet another embodiment, the fragment contains one or more complementarity determining regions (CDRs) from a light chain and/or a heavy chain of the antibody.

In another aspect, the invention provides polypeptides (which may or may not be antibodies) comprising any of the following: a) one or more CDRs (or fragments thereof) from the light or heavy chain: b) three CDRs from the light chain; c) three CDRs from the heavy chain; d) three CDRs from the light chain and three CDRs from the heavy chain; e) the light chain variable region: f) the heavy chain variable region of the anti-RAAG10 antibody.

In another aspect, the invention is a humanized antibody. In some embodiments, the humanized antibody comprises one or more CDRs of a non-human anti-RAAG10 antibody. In some embodiments, the humanized antibody binds to the same or different epitope(s) as other anti-RAAG10 antibodies. Generally, a humanized antibody of the invention comprises one or more (one, two, three, four, five, six, or fragments thereof) CDRs which are the same and/or derived from the CDR(s) of the original non-human anti-RAAG10 antibody. In some embodiments, the human antibody binds to the same or different epitope(s) as other anti-RAAG10 antibodies. In anther aspect, the invention is a chimeric antibody comprising variable regions derived from variable regions of a heavy chain and a light chain of a non-human anti-RAAG10 antibody and constant regions derived from constant regions of a heavy chain and a light chain of a human antibody.

In another aspect, the invention is an isolated polynucleotide that encodes any one of antibodies LUCA1, BLA8. PA20, or SKIN2 that is produced by a host cell with a deposit number of ATCC No. PTA-4217, PTA-4218, PTA-4244, or PTA-4245, respectively, or progeny thereof. This invention encompasses antibody polypeptides having the inherent binding or biological activities of any of the above-specified antibodies. In another aspect, the invention provides polynucleotides encoding any of the antibodies (including antibody fragments) as well as any other polypeptides described herein.

In another aspect, the invention is a pharmaceutical composition comprising any of the polypeptides (including any of the antibodies described herein) or polynucleotides described herein, such as pharmaceutical compositions comprising an anti-RAAG10 antibody linked to a chemotherapeutic agent, an antibody comprising a fragment of an anti-RAAG10 antibody, a humanized antibody of a non-human anti-RAAG10 antibody, a chimeric antibody comprising variable regions derived from variable regions of a non-human anti-RAAG10 antibody and constant regions derived from constant regions of a human antibody, or a human antibody with one or more properties of a non-human anti-RAAG10 antibody, or any of the anti-RAAG10 antibody described herein linked to a chemotherapeutic agent (such as a radioactive moiety), and a pharmaceutically acceptable excipient.

In one aspect, the invention is a composition comprising an anti-RAAG10 antibody bound to RAAG10 present on a diseased or cancerous cell. In preferred embodiments, the cancer cell is selected from the group consisting of ovarian, lung, prostate, pancreatic, colon, and breast cancer cells. In some embodiments, the cancer cell is isolated. In some embodiments, the cancer cell is in a biological sample. Generally, the biological sample is from an individual, such as a human.

In another aspect, the invention is a method of diagnosing disease in an individual by detecting RAAG10 on cells from the individual, particularly diseases or disorders associated with inflammatory or autoimmune responses in individuals. In other aspects of the invention, methods are provided for modulating inflammatory or autoimmune responses in individuals. Diseases and conditions resulting from inflammation and autoimmune disorders that may be subject to treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury.

Still other indications for therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue.

In another aspect, the invention is a method for diagnosing whether an individual has cancer, comprising determining whether there is expression of RAAG10 on selected cells from the individual, wherein the expression of RAAG10 on said cells is indicative of said cancer. In some embodiments, the expression of RAAG10 is determined using an anti-RAAG10 antibody. In some embodiments, the method involves detecting the level of RAAG10 expression from cells. The term "detection" as used herein includes qualitative and/or quantitative detection (measuring levels) with or without reference to a control.

In yet another aspect, the invention is a method of diagnosing cancer in an individual by detecting RAAG10 on or released from cells from the individual, wherein the cancer is selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, dhordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, pheochromocytoma, pituitary tumors, prostate cancer, posterious unveal melanoma, rare hematologic disorders, renal metastatic cancer, rhabdoid tumor, rhabdomyosarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In another aspect, the invention is a method for aiding diagnosis of cancer (such as but not limited to ovarian, lung, prostate, pancreatic, colon, or breast cancer) in an individual comprising determining the expression of RAAG10 in a biological sample from the individual. In some embodiments, the expression of RAAG10 is determined using an anti-RAAG10 antibody. In some embodiments, the anti-RAAG10 antibody is a family member specifically named herein. In some embodiments, the method is detecting the level of RAAG10 expression from cells.

In yet another aspect, the invention is a method of treating cancer by administering an effective amount of an antibody that binds to RAAG10 sufficient to reduce growth of cancerous cells. In some embodiments, the antibody is an anti-RAAG10 antibody. In certain embodiments, the cancerous cells are selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, dhordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancer, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, pheochromocytoma, pituitary tumors, prostate cancer, posterious unveal melanoma, rare hematologic disorders, renal metastatic cancer, rhabdoid tumor, rhabdomyosarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma). In certain preferred embodiments, the cancerous cells are selected from the group of solid tumors including but not limited to breast cancer, colon cancer, prostate cancer, lung cancer, sarcoma, renal metastatic cancer, thyroid metastatic cancer, and clear cell carcinoma.

In yet another aspect, the invention is a method of delaying development of metastasis in an individual having cancer comprising administering an effective amount of at least one of a family of antibodies that bind specifically to RAAG10. In one embodiment, the antibody is an anti-RAAG10 antibody. In another aspect, the invention is a method of inhibiting growth and/or proliferation of cancer cells in vitro or in an individual comprising administering an effective amount of a composition comprising an anti-RAAG10 antibody associated with (including linked to) a chemotherapeutic agent to the cell culture or sample, or to the individual.

In yet another aspect, the invention is a method of delivering a therapeutic agent to a cancerous cell in an individual by administering to the individual an effective amount of at least one member of a family of antibodies, which bind specifically to RAAG10. In other embodiments, an anti-RAAG10 antibody is delivered to an individual in combination with (including linked to) another therapeutic agent.

In some embodiments, the anti-RAAG10 antibody is a humanized antibody derived from a named antibody family member herein (generally, but not necessarily, comprising one or more partial or intact CDRs of the antibody). In some embodiments, the anti-RAAG10 antibody is a human antibody with one or more properties of the named antibody family member. In some embodiments, the chemotherapeutic agent (such as a toxin or a radioactive molecule) is delivered into the cancer cells (is internalized). In some embodiments, the agent is saporin.

In another aspect, the invention is a method of treating cancer in an individual comprising administering an effective amount of a composition comprising an anti-RAAG10 antibody associated with (including linked to) a chemotherapeutic agent to the individual.

The present invention further provides methods for modulating, either by enhancing or reducing, the association of RAAG10 with a cytoplasmic signaling partner. The association of RAAG10 with a cytoplasmic signaling partner can be impacted by contacting a RAAG10 molecule presenting on a cell surface, with an agent that modulates the binding of the signaling partner to RAAG10. Agents which block or reduce RAAG10 association with its binding and/or signaling partners can be used to modulate biological and pathological processes which are involved in RAAG10-mediated inflammation or immune responses. Pathological processes involving this action include tumor-associated cell growth.

Agents can be tested for their ability to block, reduce, enhance or otherwise modulate the association of RAAG10 with a binding partner, such as an anti-RAAG10 antibody. Specifically, an agent can be tested for the ability to modulate such an interaction by incubating a peptide comprising the RAAG10 interaction site (typically in its native conformation as it exists on intact living cells) with a binding partner and a test agent, and determining whether the test agent reduces or enhances the binding of the binding partner to the RAAG10 peptide. Agonists, antagonists, and other modulators are expressly contemplated.

Other aspects of this invention relate to the novel antigen identified and referred to herein as RAAG10. This antigen is suitable for use as an immunogen and for a variety of research, diagnostic and therapeutic purposes.

In certain aspects, the invention is a method for aiding in the diagnosis of disease in an individual comprising the steps of (i) assaying for the presence of RAAG10 in a blood or tissue sample obtained from an individual; (ii) detecting whether said sample has an increased amount of a RAAG10 marker relative to a normal (non-diseased) blood or tissue sample: and (iii) correlating an increased amount of said marker to a positive diagnosis or correlating the absence of an increased amount of said marker to a negative diagnosis for disease. In certain embodiments, the marker is detected using an anti-RAAG10 antibody. In certain embodiments, the method is effected by a technique selected from the group consisting of radionuclide imaging, flow cytometry, and immunohistochemistry.

DETAILED DESCRIPTION OF THE INVENTION

Figure 1:
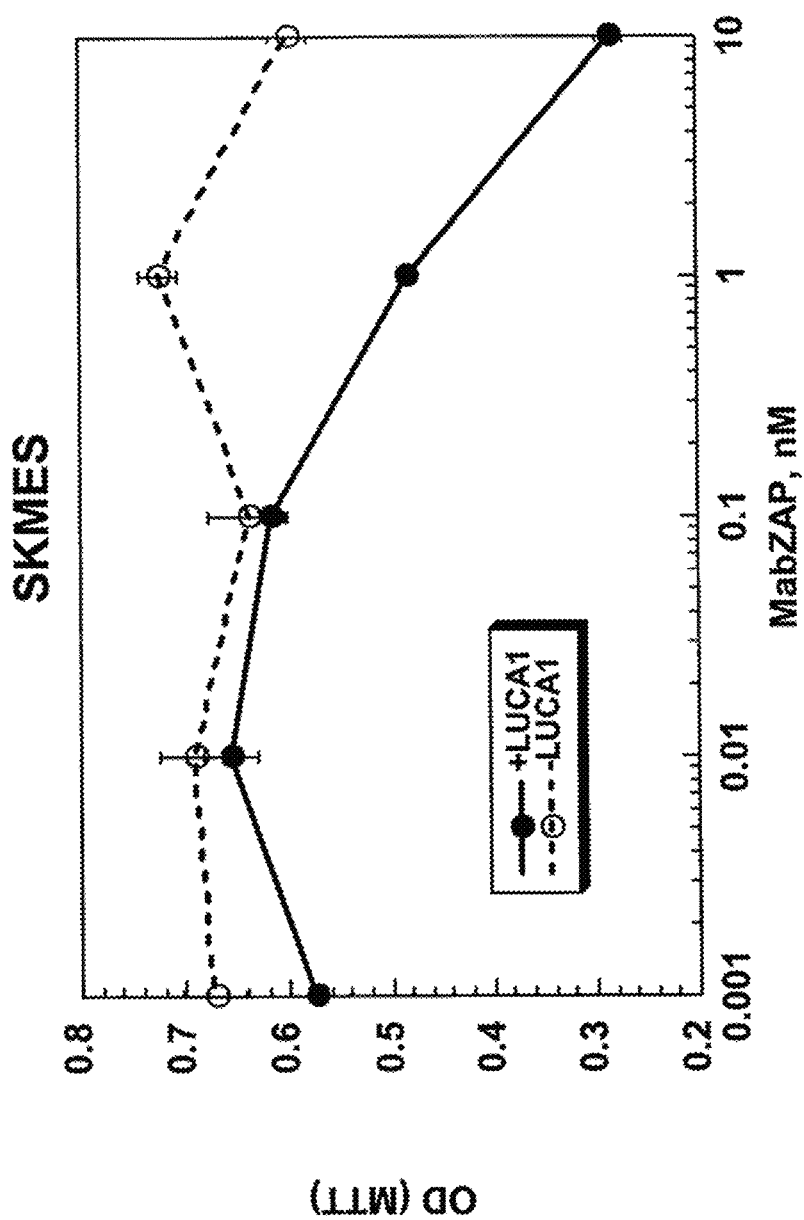
FIG. 1 shows the results of antibody internalization studies with the LUCA1 antibody. The divergence of the lines at the higher concentrations of MabZAP indicates that LUCA1 is internalized.

The invention provides a novel antigen, RAAG10, that is expressed on cancerous cells of various tissue types, including but not limited to breast, colon, lung, and prostate cancers. Further, the invention provides monoclonal antibodies and polypeptides that bind to RAAG10 and methods making and using these antibodies and polypeptides to diagnose and treat various diseases human cancers associated with expression and/or overexpression of RAAG10.

1. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; Oligonucleotide Synthesis (M. J. Gait, ed., 1984); *Methods in Molecular Biology*, Humana Press: *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons: *Method in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty, ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

"RAAG10" and "B7-H3L" refer to that novel polypeptide antigen with a glycosylated molecular weight of approximately 100 kD, against which the antibodies of the present invention are directed. As described in more detail herein, this antigen has more than one different epitope. Some of the preferred antibody embodiments of this invention are directed against one of three specific epitopes of the RAAG10 antigen. It is currently believed that RAAG10 is overexpressed in certain cancer cells in comparison to their normal tissue counterparts.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

A "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab. Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody".

"Humanized" antibodies refer to a chimeric molecule, generally prepared using recombinant techniques, having an antigen binding site derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions. This eliminates the constant region as an immunogen in human individuals, but the possibility of an immune response to the foreign variable region remains (LoBuglio, A. F. et al., (1989) Proc Natl Acad Sci USA 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable regions can be "reshaped" or "humanized" by grafting CDRs derived from nonhuman antibody on the FRs present in the human antibody to be modified. Application of this approach to various antibodies has been reported by Sato, K., et al., (1993) Cancer Res 53:851-856. Riechmann, L., et al., (1988) Nature 332:323-327: Verhoeyen, M., et al., (1988) Science 239:1534-1536: Kettleborough, C. A., et al., (1991) Protein Engineering 4:773-3783; Maeda, H., et al., (1991) Human Antibodies Hybridoma 2:124-134; Gorman, S. D., et al., (1991) Proc Natl Acad Sci USA 88:4181-4185; Tempest, P. R., et al., (1991) Bio/Technology 9:266-271; Co, M. S., et al., (1991) Proc Natl Acad Sci USA 88:2869-2873; Carter, P., et al., (1992) Proc Natl Acad Sci USA 89:4285-4289; and Co, M. S. et al., (1992) J Immunol 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a RAAG10 epitope is an antibody that binds this RAAG10 epitope with greater affinity, avidity, more readily, and/or with greater duration than it binds to other RAAG10 epitopes or non-RAAG10 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The term "immunologically active" in reference to an epitope being or "remaining immunologically active" refers to the ability of an antibody (e.g., anti-RAAG10 antibody) to bind to the epitope under different conditions, for example, after the epitope has been subjected to reducing and denaturing conditions.

Different biological functions are associated with anti-RAAG10 antibodies, including, but not limited to, ability to bind to RAAG10 (including RAAG10 on cancer cells, including but not limited to ovarian, prostate, pancreatic, lung, colon, or breast cancer cells); ability to bind to a portion of RAAG10 that is exposed on the surface of a living cell in vitro or in vivo; ability to deliver a chemotherapeutic agent to cancerous cells (such as ovarian, prostate, pancreatic, lung, colon, or breast cancer cells) expressing RAAG10; ability to deliver a therapeutic agent or detectable marker into cancer cells expressing RAAG10. As discussed herein, polypeptides (including antibodies) of the invention may have any one or more of these characteristics.

An "anti-RAAG10 equivalent antibody" or "anti-RAAG10 equivalent polypeptide" refers to an antibody or a polypeptide having one or more biological functions associated with an anti-RAAG10 antibody, such as, for example binding specificity.

As used herein, "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

Agents that are employed in the methods of this invention can be randomly selected or rationally selected or designed. As used herein, an agent is said to be randomly selected when the agent is chosen randomly without considering the specific sequences involved in the association of RAAG10 with its native binding partners or known antibodies. An example of randomly selected agents is the use of a chemical library or a peptide combinatorial library.

As used herein, an agent is said to be rationally selected or designed when the agent is chosen on a nonrandom basis that takes into account the sequence of the target site and/or its conformation in connection with the agent's action. With respect to anti-RAAG10 agents, it is currently believed that there are at least three epitopes on RAAG10 against which antibodies can be raised and therefore at least three sites of action for agents that block RAAG10/anti-RAAG10 interaction. This invention also encompasses agents which act at the sites of interaction between RAAG10 and its native binding partner, although other ligands and their active RAAG10-interactive sites are also encompassed within the scope of this invention, whether currently known or later identified. Agents can be rationally selected or rationally designed by utilizing the peptide sequences that make up the contact sites of the receptor/ligand and/or RAAG10/anti-RAAG10 antibody complex. For example, a rationally selected peptide agent can be a peptide whose amino acid sequence is identical to an epitope appearing on RAAG10 as it is exposed on the surface of a living cell in its native environment. Such an agent will reduce or block the association of the anti-RAAG10 antibody with RAAG10, or the association of RAAG10 with its native ligand, as desired, by binding to the anti-RAAG10 antibody or to the native ligand.

As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE)) to the antibody, as well as indirect labeling of the probe or antibody by reactivity with a detectable substance.

As used herein, the term "association", with regard to the antibody, includes covalent and non-covalent attachment or binding to an agent (e.g., chemotherapeutic agent). The antibody can be associated with an agent (e.g., chemotherapeutic agent) by direct binding or indirect binding via attachment to a common platform, such that the antibody directs the localization of the agent to the cancerous cell to which the antibody binds and wherein the antibody and agent do not substantially dissociate under physiological conditions such that the agent is not targeted to the same cancerous cell to which the antibody binds or such that the agent's potency is not decreased.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof, for example, cells obtained from a tissue sample collected from an individual suspected of having cancer, in preferred embodiments from ovary, lung, prostate, pancreas, colon, and breast tissue. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "delaying development of metastasis" means to defer, hinder, slow, retard, stabilize, and/or postpone development of metastasis. This delay can be of varying lengths of time, depending on the history of the cancer and/or individual being treated. As is evident to one skilled in the art, a sufficient or significant delay can, in effect, encompass prevention, in that the individual does not develop the metastasis.

An "effective amount" of a pharmaceutical composition, in one embodiment, is an amount sufficient to effect beneficial or desired results including, without limitation, clinical results such as shrinking the size of the tumor (in the cancer context, for example, breast or prostate cancer), retardation of cancerous cell growth, delaying the development of metastasis, decreasing symptoms resulting from the disease, increasing the quality of life of those suffering from the disease, decreasing the dose of other medications required to treat the disease, enhancing the effect of another medication such as via targeting and/or internalization, delaying the progression of the disease, and/or prolonging survival of individuals. An effective amount can be administered in one or more administrations. For purposes of this invention, an effective amount of drug, compound, or pharmaceutical composition is an amount sufficient to reduce the proliferation of (or destroy) cancerous cells and to reduce and/or delay the development, or growth, of metastases of cancerous cells, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages comprise 0.1 to 1.00 mg/kg/body weight. The preferred dosages comprise 1 to 100 mg/kg/body weight. The most preferred dosages comprise 10 to 100 mg/kg/body weight.

As used herein, a nucleic acid molecule or agent, antibody, composition or cell, etc., is said to be "isolated" when that nucleic acid molecule, agent, antibody, composition, or cell, etc. is substantially separated from contaminant nucleic acid molecules, antibodies, agents, compositions, or cells, etc. from its original source.

An "individual" is a vertebrate, preferably a mammal, more preferably a human. Mammals include, but are not limited to, farm animals, sport animals, pets, primates, mice and rats.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

As used herein, "substantially pure" refers to material which is at least 50% pure (i.e., free from contaminants), more preferably at least 90% pure, more preferably at least 95% pure, more preferably at least 98% pure, more preferably at least 99% pure, or greater, pure.

"Toxin" refers to any substance, which effects an adverse response within a cell. For example, a toxin directed to a cancerous cell would have an adverse, sometimes deleterious effect, on the cancerous cell. Examples of toxins include, but are not limited to, radioisotopes, calicheamicin, and maytansinoids.

As used herein, "treatment" or "treating" is an approach for obtaining beneficial or desired results including and preferably clinical results. For purposes of this invention, beneficial or desired clinical results include, but are not limited to, one or more of the following: reducing the proliferation of (or destroying) cancerous cells or other diseased, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

III. Methods of Making Antibodies

Methods of making monoclonal antibodies are known in the art. One method which may be employed is the method of Kohler and Milstein, Nature 256:495-497 (1975) or a modification thereof. Typically, monoclonal antibodies are developed in non-human species, such as mice. In general, a mouse or rat is used for immunization but other animals may also be used. The antibodies are produced by immunizing mice with an immunogenic amount of cells, cell extracts, or protein preparations that contain human RAAG10. The immunogen can be, but is not limited to, primary cells, cultured cell lines, cancerous cells, nucleic acids, or tissue. In one embodiment, human fetal bladder cells are used. In another embodiment, human pancreatic progenitor cells are used. Methods for isolating and culturing human fetal bladder cells and human pancreatic progenitor cells are detailed in Example 1. Cells used for immunogen, for example, human fetal bladder cells or human pancreatic progenitor cells, may be cultured for a period of time (at least 24 hours) prior to their use as an immunogen. Cells (e.g., human fetal bladder cells or human pancreatic progenitor cells) may be used as immunogens by themselves or in combination with a non-denaturing adjuvant, such as Ribi. In general, cells should be kept intact and preferably viable when used as immunogens. Intact cells may allow antigens to be detected better by the immunized animal than ruptured cells. Use of denaturing or harsh adjuvants, e.g., Freud's adjuvant, may rupture the human fetal bladder cells or human pancreatic progenitor cells and therefore is discouraged. The immunogen may be administered multiple times at periodic intervals such as, bi-weekly, or weekly, or may be administered in such a way as to maintain viability in the animal (e.g., in a tissue recombinant). Example 2 describes methods used to generate anti-RAAG10 antibodies and may be used to generate other monoclonal antibodies, which bind to RAAG10.

In one embodiment, monoclonal antibodies, which bind to RAAG10 are obtained by using host cells which overexpress RAAG10 as an immunogen.

To monitor the antibody response, a small biological sample (e.g., blood) may be obtained from the animal and tested for antibody titer against the immunogen. The spleen and/or several large lymph nodes can be removed and dissociated into single cells. If desired, the spleen cells may be screened (after removal of non-specifically adherent cells) by applying a cell suspension to a plate or to a well coated with the antigen. B-cells, expressing membrane-bound immunoglobulin specific for the antigen, will bind to the plate, and are not rinsed away with the rest of the suspension. Resulting B-cells, or all dissociated spleen cells, can then be fused with myeloma cells (e.g., X63-Ag8.653 and those from the Salk Institute, Cell Distribution Center, San Diego, Calif.). Polyethylene glycol (PEG) may be used to fuse spleen or lymphocytes with myeloma cells to form a hybridoma. The hybridoma is then cultured in a selective medium (e.g., hypoxanthine, aminopterin, thymidine medium, otherwise known as "HAT medium"). The resulting hybridomas are then plated by limiting dilution, and are assayed for the production of antibodies that bind specifically to the immunogen (e.g., surface of the HFB cells, surface of cancer cell lines, fetal bladder sections, etc.) using FACS or immunohistochemistry (IHC screening). The selected monoclonal antibody-secreting hybridomas are then cultured either in vitro (e.g., in tissue culture bottles or hollow fiber reactors), or in vivo (e.g., as ascites in mice). Example 3 provides further details about the methods utilized to obtain and screen an anti-RAAG10 antibody.

As another alternative to the cell fusion technique, EBV immortalized B cells may be used to produce monoclonal antibodies of the subject invention. The hybridomas are expanded and subcloned, if desired, and supernatants are assayed for anti-immunogen activity by conventional assay procedures (e.g., FACS, IHC, radioimmunoassay, enzyme immunoassay, fluorescence immunoassay, etc.).

In another alternative, monoclonal antibody anti-RAAG10 and any other equivalent antibodies can be sequenced and produced recombinantly by any means known in the art (e.g., humanization, use of transgenic mice to produce fully human antibodies, phage display technology, etc.). In one embodiment, anti-RAAG10 monoclonal antibody is sequenced and the polynucleotide sequence is then cloned into a vector for expression or propagation. The sequence encoding the antibody of interest may be maintained in a vector in a host cell and the host cell can then be expanded and frozen for future use.

The polynucleotide sequence of monoclonal antibody anti-RAAG10 and any other equivalent antibodies may be used for genetic manipulation to generate a "humanized" antibody, to improve the affinity, or other characteristics of the antibody. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; and 6,331,415.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. *Nature* 349:293-299 (1991), Lobuglio et al. *Proc. Nat. Acad. Sci. USA* 86:4220-4224 (1989), Shaw et al. *J Immunol.* 138:4534-4538 (1987), and Brown et al. *Cancer Res.* 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988), Verhoeyen et al. *Science* 239:1534-1536 (1988), and Jones et al. *Nature* 321:522-525 (1986). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules which limits the duration and effectiveness of therapeutic applications of those moieties in human recipients. Other methods of humanizing antibodies that may also be utilized are disclosed by Daugherty et al., *Nucl. Acids Res.*, 19:2471-2476 (1991) and in U.S. Pat. Nos. 6,180,377; 6,054,297; 5,997,867; and 5,866,692.

The invention also encompasses single chain variable region fragments ("scFv") of antibodies of this invention, such as mKID2. Single chain variable region fragments are made by linking light and/or heavy chain variable regions by using a short linking peptide. Bird et al. (1988) *Science* 242: 423-426 describes example of linking peptides which bridge approximately 3.5 nm between the carboxy terminus of one variable region and the amino terminus of the other variable region. Linkers of other sequences have been designed and used, Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention includes modifications to antibodies, including functionally equivalent antibodies and polypeptides that do not significantly affect their properties and variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention also encompasses fusion proteins comprising one or more fragments or regions from the antibodies of this invention. In one embodiment, a fusion polypeptide is provided that comprises at least 10 contiguous amino acids of variable light chain region and at least 10 amino acids of variable heavy chain region. In another embodiment, the fusion polypeptide contains a heterologous immunoglobulin constant region. In another embodiment, the fusion polypeptide contains a light chain variable region and a heavy chain variable region of an antibody produced from a hybridoma deposited with the ATCC as described herein. For purposes of this invention, an antibody fusion protein contains one or more anti-RAAG10 polypeptides and another amino acid sequence to which it is not attached in the native molecule, for example, a heterologous sequence or a homologous sequence from another region. An anti-RAAG10 polypeptide can be created by methods known in the art, for example, synthetically or recombinantly.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Methods for expressing antibodies recombinantly in plants or milk have been disclosed. See, for example, Peeters, et al. (2001) *Vaccine* 19:2756; Lonberg, N. and D. Huszar (1995) *Int. Rev. Immunol* 13:65; and Pollock, et al. (1999) *J Immunol Methods* 231:147. Methods for making derivatives of antibodies, e.g., humanized, single chain, etc. are known in the art. In another alternative, antibodies may be made recombinantly by phage display technology. See, for example, U.S. Pat. Nos. 5,565,332; 5,580,717; 5,733,743; 6,265,150; and Winter et al., *Annu. Rev. Immunol.* 12:433-455 (1994).

The antibodies or protein of interest may be subjected to sequencing by Edman degradation, which is well-known to those of skill in the art. The peptide information generated from mass spectrometry or Edman degradation can be used to design probes or primers that are used to clone the protein of interest.

An alternative method of cloning the protein of interest is by "panning" using ALCAM for cells expressing the antibody or protein of interest. The "panning" procedure is conducted by obtaining a cDNA library from tissues or cells that express the antibody or protein of interest, over-expressing the cDNAs in a second cell type, and screening the transfected cells of the second cell type for a specific binding to ALCAM. Detailed descriptions of the methods used in cloning mammalian genes coding for cell surface proteins by "panning" can be found in the art. See, for example, Aruffo, A. and Seed, B. *Proc. Natl. Acad. Sci. USA*, 84, 8573-8577 (1987) and Stephan, J. et al., Endocrinology 140: 5841-5854 (1999).

cDNAs can be obtained by reverse transcribing the mRNAs from a particular cell type according to standard methods in the art. Specifically, mRNA can be isolated using various lytic enzymes or chemical solutions according to the procedures set forth in Sambrook, et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment: lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to RAAG10 is effected by an immunoassay or FACS. A cell overexpressing the antibody or protein of interest can be identified.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an anti-RAAG10 polypeptide could be produced by an automated polypeptide synthesizer employing the solid phase method.

IV. Methods for Screening Monoclonal Antibodies

Several methods may be used to screen monoclonal antibodies that bind to RAAG10. It is understood that "binding" refers to immunologically relevant binding, i.e., binding which is specific for the unique antigen for which the immunoglobulin molecule is encoded. It does not refer to non-specific binding that may occur when an immunoglobulin is used at a very high concentration against a non-specific target. In one embodiment, monoclonal antibodies are screened for binding to RAAG10 using standard screening techniques. In this manner, anti-RAAG10 monoclonal antibody was obtained. In accordance with the Budapest Treaty, the hybridomas which produce anti-RAAG10 monoclonal antibodies have been deposited in the American Type Culture Collection (ATCC) 10801 University Blvd., Manassas Va. 20110-2209 on Apr. 9, 2002 with a Patent Deposit Designation of PTA-4217, PTA-4218, PTA-4244, and PTA-4245.

Monoclonal antibodies that bind to RAAG10 are screened for binding to cancerous tissues and non-cancerous cells. In one embodiment, monoclonal antibodies which bind to RAAG10 and that are also cross reactive to human cancerous cells or tissues, but not to normal cells or tissues to the same degree, are selected. One method which may be employed for screening is immunohistochemistry (IHC). Standard immunohistochemical techniques are known to those of average skill in the art. See, for example, *Animal Cell Culture Method* (J. P. Mather and D. Barnes, eds., Academic Press, Vol. 57, Ch. 18 and 19, pp. 314-350, 1998). Biological samples (e.g., tissues) may be obtained from biopsies, autopsies, or necropsies. To ascertain if RAAG10 is present only on cancerous cells, anti-RAAG10 antibodies may be used to detect the presence of RAAG10 on tissues from individuals with cancer while other non-cancerous tissues from the individual suffering from cancer or tissues from individuals without cancer are used as a control. The tissue can be embedded in a solid or semi-solid substance that prevents damage during freezing (e.g. agarose gel or OCT) and then sectioned for staining. Cancers from different organs and at different grades can be used to screen monoclonal antibodies. Examples of tissues that may be used for screening purposes include but are not limited to ovary, breast, lung, prostate, colon, kidney, skin, thyroid, brain, heart, liver, stomach, nerve, blood vessels, bone, upper digestive tract, and pancreas. Examples of different cancer types that may be used for screening purposes include but are not limited to carcinomas, adenocarcinomas, sarcomas, adenosarcomas, lymphomas, and leukemias.

In yet another alternative, cancerous cells lines such as SK-Ov-3 (ATCC #HTB 77), LnCap (ATCC #CRL-1740), A549 (ATCC #CCL 185), PANC-1 (ATCC #CRL 1469), SK-BR-3 (ATCC #HTB 30), SK-MES-1 (ATCC #HTB 58), HT-29 (HTB-38), SW 480 (ATCC #CCL 228), AsPC-1 (ATCC #CRL 1682), Capan-1 (ATCC #HTB 79), CFPAC-1 (ATCC #CRL 1918), HPAF-II (ATCC #CRL-1997), Hs-700T (ATCC #HTB 147), ES-2 (ATCC #CRL-1978), PC-3 (ATCC #CRL 1435), Du-145 (ATCC #HTB-81). Calu3 (ATCC #HTB-55), A498 (ATCC #CRL-7908), Caki-2 (ATCC #HTB-47), 786-O (ATCC #CRL-1932), Hs 766T (ATCC #HTB-134), MCF7 (ATCC #HTB-22), BT-474 (ATCC #HTB-20), Rav CA130 (proprietary lung cancer line developed at Raven Biotechnologies, inc.), Rav9926 (proprietary pancreatic cancer cell line developed at Raven), and 22Rv1 (ATCC #CRL-2505) and normal cells from their respective tissues may be used to screen for monoclonal antibodies which are specific for cancerous tissue. Primary, or low passage, cell cultures derived from normal tissues from different organs, including but not limited to, ovary, breast, lung, prostate, colon, kidney, skin, thyroid, aortic smooth muscle, and endothelial cells can be used as negative controls. The cancerous or non-cancerous cells can be grown on glass slides or coverslips, or on plastic surfaces, or prepared in a CellArray™, as described in WO 01/43869, and screened for the binding of antibody using IHC as described above for tissues. Alternatively, cells may be removed from the growth surface using non-proteolytic means and spun into a pellet, which is then embedded and treated as tissues for IHC analysis as described above. In another alternative, single cells may be screened by incubating with the primary antibody, a secondary "reporter" antibody linked to a fluorescent molecule and then analyzed using a fluorescent activated cell sorting (FACS) machine.

Several different detection systems may be utilized to detect binding of antibodies to tissue section. Typically, immunohistochemistry involves the binding of a primary antibody to the tissue and then a secondary antibody reactive against the species from the primary antibody was generated and conjugated to a detectable marker (e.g., horseradish peroxidase, HRP, or diaminobenzidine, DAB). One alternative method that may be used is polyclonal mirror image complementary antibodies or polyMICA. PolyMICA (polyclonal Mirror Image Complementary Antibodies) technique, described by D. C. Mangham and P. G. Isaacson (*Histopathology* (1999) 35(2):129-33), can be used to test binding of primary antibodies (e.g., anti-RAAG10 antibodies) to normal and cancerous tissue. Several kinds of polyMICA™ Detection kits are commercially available from The Binding Site Limited (P.O. Box 4073 Birmingham B29 6AT England). Product No. HK004.D is a polyMICA™ Detection kit which uses DAB chromagen. Product No. HK004.A is a polyMICA™ Detection kit which uses AEC chromagen. Alternatively, the primary antibody may be directly labeled with the detectable marker.

The first step in HC screening to select for an appropriate antibody is the binding of primary antibodies raised in mice (e.g., anti-RAAG10 antibodies) to one or more immunogens (e.g., cells or tissue samples). In one embodiment, the tissue sample is sections of frozen tissue from different organs. The cells or tissue samples can be either cancerous or non-cancerous.

Frozen tissues can be prepared, sectioned, with or without fixation, and IHC performed by any of a number of methods known to one familiar with the art. See, for example, Stephan et al. *Dev. Biol.* 212: 264-277 (1999), and Stephan et al. *Endocrinology* 140: 5841-54 (1999).

V. Methods of Characterizing Anti-RAAG10 Antibodies

Several methods can be used to characterize anti-RAAG10 antibodies. One method is to identify the epitope to which it binds. Epitope mapping is commercially available from various sources, for example, Pepscan Systems (Edelhertweg 15, 8219 PH Lelystad, The Netherlands). Epitope mapping can be used to determine the sequence to which an anti-RAAG10 antibody binds. The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with anti-RAAG10 antibody. The epitope to which anti-RAAG10 antibody binds can be determined in a systematic screening by using overlapping peptides derived from the extracellular sequence and determining binding by anti-RAAG10 antibody. Epitope mapping of RAAG10 is detailed in the Examples. We have determined that more than one RAAG10 epitope exists, with our antibodies KID13, LUCA1 and GB8 binding to one epitope, our antibodies SKIN2, PA20, and KID1 binding to a second epitope, and our antibody BLA8 binding to a third epitope. These antibodies are merely representative of the groups of novel antibodies with similar inherent binding and biological characteristics, all of which are specifically encompassed within the scope of this invention.

Yet another method which can be used to characterize an anti-RAAG10 antibody is to use competition assays with other antibodies known to bind to the same antigen, i.e., RAAG10 to determine if anti-RAAG10 antibodies binds to the same epitope as other antibodies. Examples of commercially available antibodies to RAAG10 may be available and may be identified using the binding assays taught herein. Competition assays are well known to those of skill in the an, and such procedures and illustrative data are detailed further in the Examples. Anti-RAAG10 antibodies can be further characterized by the tissues, type of cancer or type of tumor to which they bind.

Another method of characterizing anti-RAAG10 antibodies is by the antigen to which it binds. Anti-RAAG10 antibodies were used in Western blots with cell lysates from various human cancers. As is known to one of skill in the art. Western blotting can involve running cell lysates and/or cell fractions on a denaturing or non-denaturing gel, transferring the proteins to nitrocellulose paper, and then probing the blot with an antibody (e.g., anti-RAAG10 antibody) to see which proteins are bound by the antibody. This procedure is detailed further in Example 4. The band to which anti-RAAG10 antibody bound was isolated and further analyzed using mass spectroscopy, as described in Examples 5 and 6. The antigen to which anti-RAAG10 antibody binds was found to be RAAG10. RAAG10 is associated with various human cancers of different tissues including but not limited to colon, lung, breast, prostate, ovary, pancreas, kidney as well as other types of cancer such as sarcoma. Further description of RAAG10 is given in Example 6 and 7.

VI. Methods of Diagnosing Cancer Using Anti-RAAG10 Antibodies

Monoclonal antibodies to RAAG10 made by the methods disclosed herein may be used to identify the presence or absence of cancerous cells in a variety of tissues, including but not limited to, ovary, breast, lung, prostate, colon, kidney, pancreas, skin, thyroid, brain, heart, liver, stomach, nerve, blood vessels, bone, and upper digestive tract, for purposes of diagnosis. Monoclonal antibodies to RAAG10 made by the methods disclosed herein may also be used to identify the presence or absence of cancerous cells, or the level thereof, which are circulating in blood after their release from a solid tumor. Such circulating antigen may be an intact RAAG10 antigen, or a fragment thereof that retains the ability to be detected according to the methods taught herein. Such detection may be effected by FACS analysis using standard methods commonly used in the art.

These uses can involve the formation of a complex between RAAG10 and an antibody that binds specifically to RAAG10. Examples of such antibodies include but are not limited to those anti-RAAG10 monoclonal antibodies produced by the hybridomas deposited in the ATCC with the designations PTA-4217, PTA-4218, PTA-4244, and PTA-4245. The formation of such a complex can be in vitro or in vivo. Without being bound by theory, monoclonal antibody anti-RAAG10 can bind to RAAG10 through the extracellular domain of RAAG10 and may then be internalized.

In a preferred embodiment of the diagnostic methods of this invention, the antibody bears a detectable label. Examples of labels that may be used include a radioactive agent or a fluorophore, such as fluoroisothiocyanate or phycoerythrin.

As with other known antibodies used commercially for diagnostic and therapeutic purposes, the target antigen of this invention is broadly expressed in normal tissue. It is also upregulated in some tumors. Therefore, the particular dosages and routes of delivery of the antibodies of this invention as used for diagnostic or therapeutic agents will be tailored to the particular tumor or disease state at hand, as well as to the particular individual being treated.

One method of using the antibodies for diagnosis is in vivo tumor imaging by linking the antibody to a radioactive or radioopaque agent, administering the antibody to the individual and using an x-ray or other imaging machine to visualize the localization of the labeled antibody at the surface of cancer cells expressing the antigen. The antibody is administered at a concentration that promotes binding at physiological conditions.

In vitro techniques for detection of RAAG10 are routine in the art and include enzyme linked immunosorbent assays (ELISAs), immunoprecipitations, immunofluorescence, enzyme immunoassay (EIA), radioimmunoassay (RIA), and Western blot analysis.

In aspects of this invention, methods of radioimaging of tumours or neoplasms, or of measuring the effectiveness of a method of treatment with a radiolabelled antibody, comprising the step of administering a radiolabelled, tumour-specific antibody to an individual following the practice of this invention. The radiolabelled antibody may be a monoclonal or polyclonal antibody comprising a radiolabel, preferably selected from the group consisting of Technetium-99m, Indium-111, Iodine-131, Rhenium-186, Rhenium-188, Samarium-153, Lutetium-177, Copper-64, Scandium-47, Yttrium-90. Monoclonal antibodies labelled with therapeutic radionuclides such as Iodine-131, Rhenium-188, Holmium-166, Samarium-153 and Scandium-47, which do not compromise the immunoreactivity of antibodies and are not broken down in vivo, are especially preferred. The person skilled in the art will appreciate that other radioactive isotopes are known, and may be suitable for specific applications. The radioimaging may be conducted using Single Photon Emission Computer Tomography (SPECT), Position Emmission Tomography (PET), Computer Tomography (CT) or Magnetic Resonance Imaging (MRI). Correlative imaging, which permits greater anatomical definition of location of metastases located by radioimmunoimaging, is also contemplated.

In other methods, the cancerous cells are removed and the tissue prepared for immunohistochemistry by methods well known in the art (e.g., embedding in a freezing compound, freezing and sectioning, with or without fixation; fixation and paraffin embedding with or without various methods of antigen retrieval and counterstaining). The monoclonal antibodies may also be used to identify cancerous cells at different stages of development. The antibodies may also be used to determine which individuals' tumors express the antigen on their surface at a pre-determined level and are thus candidates for immunotherapy using antibodies directed against said antigen. The antibodies may recognize both primary and metastasizing cancers of the ovary, prostate and pancreas and primary cancers of the lung that express RAAG10. As used herein, detection may include qualitative and/or quantitative detection and may include comparing the level measured to a normal cell for an increased level of expression of RAAG10 in cancerous cells.

The invention also provides methods of aiding diagnosis of cancer (such as ovarian, lung, pancreatic, prostate, colon, or breast cancer) in an individual using any antibody that binds to RAAG10 and any other methods that can be used determine the level of RAAG10 expression. As used herein, methods for "aiding diagnosis" means that these methods assist in making a clinical determination regarding the classification, or nature, of cancer, and may or may not be conclusive with respect to the definitive diagnosis. Accordingly, a method of aiding diagnosis of cancer can comprise the step of detecting the level of RAAG10 in a biological sample from the individual and/or determining the level of RAAG10 expression in the sample. Antibodies recognizing the antigen may also be used to create diagnostic immunoassays for detecting antigen released or secreted from living or dying cancer cells in bodily fluids, including but not limited to, blood, saliva, urine, pulmonary fluid, or ascites fluid.

Not all cells in a particular tumor of interest will express RAAG10, and cancerous cells in other tissues may express RAAG10, thus an individual should be screened for the presence or absence of RAAG10 on cancerous cells to determine the usefulness of immunotherapy in the individual. The anti-RAAG10 antibodies made by the methods disclosed herein may be used to determine whether an individual diagnosed with cancer may be deemed a candidate for immunotherapy using antibodies directed against RAAG10. In one embodiment, a cancerous tumor or a biopsy sample may be tested for expression of RAAG10, using antibodies directed against RAAG10. Individuals with cancer cells that express RAAG10 are suitable candidates for immunotherapy using antibodies directed against RAAG10. Staining with anti-RAAG10 antibody may also be used to distinguish cancerous tissues from normal tissues.

Methods of using anti-RAAG10 antibodies for diagnostic purposes are useful both before and after any form of anti-cancer treatment. e.g., chemotherapy or radiation therapy, to determine which tumors are most likely to respond to a given treatment, prognosis for individual with cancer, tumor subtype or origin of metastatic disease, and progression of the disease or response to treatment.

The compositions of this invention are also suitable for diagnosis of disease states other than cancer, using the methods generally described above in application with other diseased (non-cancerous) cells. Disease states suitable for use in the methods of this invention include, but are not limited to, diseases or disorders associated with inflammatory or autoimmune responses in individuals. The methods described above may be used for modulating inflammatory or autoimmune responses in individuals. Diseases and conditions resulting from inflammation and autoimmune disorders that may be subject to diagnosis and/or treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury.

Still other indications for diagnostic and/or therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue.

VII. Compositions of This Invention

This invention also encompasses compositions, including pharmaceutical compositions, comprising anti-RAAG10 antibodies, polypeptides derived from anti-RAAG10 antibodies, polynucleotides comprising sequence encoding anti-RAAG10 antibodies, and other agents as described herein. As used herein, compositions further comprises one or more antibodies, polypeptides and/or proteins that bind to RAAG10, and/or one or more polynucleotides comprising sequences encoding one or more antibodies, polypeptides and proteins that bind to RAAG10.

The antibodies, agents, polypeptides and proteins of this invention are further identified and characterized by any (one or more) of the following criteria: (a) ability to bind to RAAG10 (including RAAG10 on cancer cells, including but not limited to ovarian, prostate, pancreatic, lung, colon, or breast cancer cells); (b) ability to competitively inhibits preferential binding of a known anti-RAAG10 antibody to RAAG10, including the ability to preferentially bind to the same RAAG10 epitope to which the original antibody preferentially binds; (c) ability to bind to a portion of RAAG10 that is exposed on the surface of a living cell in vitro or in vivo; (d) ability to bind to a portion of RAAG10 that is exposed on the surface of living cancer cells, such as but not limited to ovarian, prostate, pancreatic, lung, colon, or breast cancer cells; (e) ability to deliver a chemotherapeutic agent or detectable marker to cancerous cells (such as but not limited to ovarian, prostate, pancreatic, lung, colon, or breast cancer cells) expressing ALCAM; (f) ability to deliver a therapeutic agent into cancerous cells (such as but not limited to ovarian cancer cells) expressing RAAG10.

In some embodiments, the antibody of the invention is an antibody that is produced by a host cell with a deposit number of any one of ATCC Nos. PTA-4217, 4218, 4244, or 4245, or progeny thereof. The present invention also encompasses various formulations of antibodies produced by these deposited hybridomas and equivalent antibodies or polypeptide fragments (e.g., Fab, Fab', F(ab')$_2$, Fv, Fc, etc.), chimeric antibodies, single chain (ScFv), mutants thereof, fusion proteins comprising an antibody portion, humanized antibodies, and any other modified configuration of any of these or equivalent antibodies that comprises an antigen (RAAG10), recognition site of the required specificity. The invention also provides human antibodies displaying one or more of the biological characteristics of an anti-RAAG10 family member. The equivalent antibodies of the anti-RAAG10 family (including humanized antibodies and human antibodies), polypeptide fragments, and polypeptides comprising any of these fragments are identified and characterized by any (one or more) of the five criteria described above.

In some embodiments, the antibodies, polypeptides and proteins of the invention that bind to RAAG10 are antibodies, polypeptides and proteins that competitively inhibit preferential binding of a herein-specified anti-RAAG10 antibody to RAAG10. In some embodiments, the antibodies, the polypeptides and the proteins preferentially bind to the same epitope on RAAG10 as one of the antibodies LUCA1, BLA8, PA20, and SKIN2 preferentially binds.

Accordingly, the invention provides any of the following (or compositions, including pharmaceutical compositions, comprising any of the following); (a) an antibody produced by the host cell with a deposit number identified above or its progeny; (b) a humanized form of such an antibody; (c) an antibody comprising one or more of the light chain and/or heavy chain variable regions of such an antibody; (d) a chimeric antibody comprising variable regions homologous or derived from variable regions of a heavy chain and a light chain of such an antibody, and constant regions homologous or derived from constant regions of a heavy chain and a light chain of a human antibody; (e) an antibody comprising one or more of the light chain and/or heavy chain CDRs (at least one, two, three, four, five, or six) of such an antibody; (f) an antibody comprising a heavy and/or a light chain of such an antibody; (g) a human antibody that is equivalent to such an antibody. A humanized form of the antibody may or may not have CDRs identical to that original antibody, or antibody produced by a host cell with a deposit number identified above. Determination of CDR regions is well within the skill of the art. In some embodiments, the invention provides an antibody which comprises at least one CDR that is substantially homologous to at least one CDR, at least two, at least three, at least four, at least 5 CDRs of an antibody produced by one of the above-identified deposited hybridomas (or, in some embodiments substantially homologous to all 6 CDRs of one of these antibodies, or derived from one of these antibodies), or antibody produced by the host cell with a deposit number identified above. Other embodiments include antibodies that have at least two, three, four, five, or six CDR(s) that are substantially homologous to at least two, three, four, five or six CDRs of an antibody produced from a hybridoma deposited as identified herein, or derived from such an antibody. It is understood that, for purposes of this invention, binding specificity and/or overall activity (which may be in terms of delivering a chemotherapeutic agent to or into cancerous cells to reduce the growth and/or proliferation of cancer cells, to induce apoptotic cell death in the cancer cell, to delay the development of metastasis, and/or treating palliatively) is generally retained, although the extent of activity may vary compared to an antibody produced by a deposited hybridoma (may be greater or lesser). The invention also provides methods of making any of these antibodies. Methods of making antibodies are known in the art and are described herein.

The invention also provides polypeptides comprising an amino acid sequence of the antibodies of the invention. In some embodiments, the polypeptide comprises one or more of the light chain and/or heavy chain variable regions of the antibody. In some embodiments, the polypeptide comprises one or more of the light chain and/or heavy chain CDRs of the antibody. In some embodiments, the polypeptide comprises three CDRs of the light chain and/or heavy chain of the antibody. In some embodiments, the polypeptide comprises an amino acid sequence of the antibody that has any of the following: at least 5 contiguous amino acids of a sequence of the original antibody, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of the antibody. In one embodiment, the variable region is from a light chain of the original antibody. In another embodiment, the variable region is from a heavy chain of the antibody. In another embodiment, the 5 (or more) contiguous amino acids are from a complementarity determining region (CDR) of the antibody.

VIII. Methods of Using Anti-RAAG10 Antibodies for Therapeutic Purposes

Monoclonal antibodies to RAAG10 may be used for therapeutic purposes in individuals with cancer or other diseases. Therapy with anti-RAAG10 antibodies can involve formation of complexes both in vitro and in vivo as described above. In one embodiment, monoclonal antibody anti-RAAG10 can bind to and reduce the proliferation of cancerous cells. It is understood that the antibody is administered at a concentration that promotes binding at physiological (e.g., in vivo) conditions. In another embodiment, monoclonal antibodies to RAAG10 can be used for immunotherapy directed at cancerous cells of different tissues such as colon, lung, breast, prostate, ovary, pancreas, kidney and other types of cancer such as sarcoma. In another embodiment, monoclonal antibody anti-RAAG10 alone can bind to and induce apoptotic cell death in the cancer cell. In another embodiment, monoclonal antibody anti-RAAG10 can bind to cancerous cells and delay the development of metastasis. In yet another embodiment, an individual with cancer is given palliative treatment with anti-RAAG10 antibody. Palliative treatment of a cancer individual involves treating or lessening the adverse symptoms of the disease, or iatrogenic symptoms resulting from other treatments given for the disease without directly affecting the cancer progression. This includes treatments for easing of pain, nutritional support, sexual problems, psychological distress, depression, fatigue, psychiatric disorders, nausea, vomiting, etc.

In such situations, the anti-RAAG10 antibody may be administered with agents that enhance or direct an individual's own immune response, such as an agent that strengthens ADCC.

In yet another embodiment, anti-RAAG10 antibody be conjugated to or associated with a radioactive molecule, toxin (e.g., calicheamicin), chemotherapeutic molecule, liposomes or other vesicles containing chemotherapeutic compounds and administered to an individual in need of such treatment to target these compounds to the cancer cell containing the antigen recognized by the antibody and thus eliminate cancerous or diseased cells. Without being limited to any particular theory, the anti-RAAG10 antibody is internalized by the cell bearing RAAG10 at its surface, thus delivering the conjugated moiety to the cell to induce the therapeutic effect. In yet another embodiment, the antibody can be employed as adjuvant therapy at the time of the surgical removal of a cancer expressing the antigen in order to delay the development of metastasis. The antibody can also be administered before surgery (neoadjuvant therapy) in an individual with a tumor expressing the antigen in order to decrease the size of the tumor and thus enable or simplify surgery, spare tissue during surgery, and/or decrease the resulting disfigurement.

Chemotherapeutic agents include radioactive molecules, toxins, also referred to as cytotoxins or cytotoxic agents, which includes any agent that is detrimental to the viability of cancerous cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine. 6-thioguanine, actinomycin D, adriamycin, aldesleukin, alkylating agents, allopurinol sodium, altretamine, amifostine, anastrozole, anthramycin (AMC)), antimitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine. Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin alfa, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon alfa-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In a preferred embodiment, the cytotoxin is especially effective in dividing or rapidly dividing cells, such that non-dividing cells are relatively spared from the toxic effects.

The antibodies of the invention can be internalized within the diseased or carcinoma cells to which they bind and are therefore particularly useful for therapeutic applications, for example, delivering into the cells toxins that need to be internalized for their adverse activity. Examples of such toxins include, but are not limited to, saporin, calicheamicin, auristatin, and maytansinoid.

The antibodies or polypeptides of the invention can be associated (including conjugated or linked) to a radioactive molecule, a toxin, or other therapeutic agents, or to liposomes or other vesicles containing therapeutic agents covalently or non-covalently, directly or indirectly. The antibody may be linked to the radioactive molecule, the toxin, or the chemotherapeutic molecule at any location along the antibody so long as the antibody is able to bind its target RAAG10.

A toxin or a chemotherapeutic agent may be coupled (e.g., covalently bonded) to a suitable monoclonal antibody either directly or indirectly (e.g., via a linker group, or, alternatively, via a linking molecule with appropriate attachment sites, such as a platform molecule as described in U.S. Pat. No. 5,552,391). The toxin and chemotherapeutic agent of the present invention can be coupled directly to the particular targeting proteins using methods known in the art. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies or polypeptides can also be linked to a chemotherapeutic agent via a microcarrier. Microcarrier refers to a biodegradable or a non-biodegradable particle which is insoluble in water and which has a size of less than about 150, 120 or 100 µm in size, more commonly less than about 50-60 µm, preferably less than about 10, 5, 2.5, 2 or 1.5 µm. Microcarriers include "nanocarriers", which are microcarriers have a size of less than about 1 µm, preferably less than about 500 nm. Such particles are known in the art. Solid phase microcarriers may be particles formed from biocompatible naturally occurring polymers, synthetic polymers or synthetic copolymers, which may include or exclude microcarriers formed from agarose or cross-linked agarose, as well as other biodegradable materials known in the art. Biodegradable solid phase microcarriers may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5]undecane (DETOSU) or poly(anhydrides), such as poly(anhydrides) of sebacic acid) under mammalian physiological conditions. Microcarriers may also be liquid phase (e.g., oil or lipid based), such liposomes, iscoms (immune-stimulating complexes, which are stable complexes of cholesterol, and phospholipid, adjuvant-active saponin) without antigen, or droplets or micelles found in oil-in-water or water-in-oil emulsions, provided the liquid phase microcarriers are biodegradable. Biodegradable liquid phase microcarriers typically incorporate a biodegradable oil, a number of which are known in the art, including squalene and vegetable oils. Microcarriers are typically spherical in shape, but microcarriers that deviate from spherical shape are also acceptable (e.g., ellipsoid, rod-shaped, etc.). Due to their insoluble nature (with respect to water), microcarriers are filterable from water and water-based (aqueous) solutions.

The antibody or polypeptide conjugates of the present invention may include a bifunctional linker that contains both a group capable of coupling to a toxic agent or chemotherapeutic agent and a group capable of coupling to the antibody. A linker can function as a spacer to distance an antibody from an agent in order to avoid interference with binding capabilities. A linker can be cleavable or non-cleavable. A linker can also serve to increase the chemical reactivity of a substituent on an agent or an antibody, and thus increase the coupling efficiency. An increase in chemical reactivity may also facilitate the use of agents, or functional groups on agents, which otherwise would not be possible. The bifunctional linker can be coupled to the antibody by means that are known in the art. For example, a linker containing an active ester moiety, such as an N-hydroxysuccinimide ester, can be used for coupling to lysine residues in the antibody via an amide linkage. In another example, a linker containing a nucleophilic amine or hydrazine residue can be coupled to aldehyde groups produced by glycolytic oxidation of antibody carbohydrate residues. In addition to these direct methods of coupling, the linker can be indirectly coupled to the antibody by means of an intermediate carrier such as an aminodextran. In these embodiments the modified linkage is via either lysine, carbohydrate, or an intermediate carrier. In one embodiment, the linker is coupled site-selectively to free thiol residues in the protein. Moieties that are suitable for selective coupling to thiol groups on proteins are well known in the art. Examples include disulfide compounds, α-halocarbonyl and α-halocarboxyl compounds, and maleimides. When a nucleophilic amine function is present in the same molecule as an α-halo carbonyl or carboxyl group the potential exists for cyclization to occur via intramolecular alkylation of the amine. Methods to prevent this problem are well known to one of ordinary skill in the art, for example by preparation of molecules in which the amine and α-halo functions are separated by inflexible groups, such as aryl groups or trans-alkenes, that make the undesired cyclization stereochemically disfavored. See, for example, U.S. Pat. No. 6,441,163 for preparation of conjugates of maytansinoids and antibody via a disulfide moiety.

One of the cleavable linkers that can be used for the preparation of antibody-drug conjugates is an acid-labile linker based on cis-aconitic acid that takes advantage of the acidic environment of different intracellular compartments such as the endosomes encountered during receptor mediated endocytosis and the lysosomes. See, for example, Shen et al., *Biochem. Biophys. Res. Commun.* 102:1048-1054 (1981) for the preparation of conjugates of daunorubicin with macromolecular carriers; Yang et al., *J. Natl. Canc. Inst.* 80:1154-1159 (1988) for the preparation of conjugates of daunorubicin to an anti-melanoma antibody; Dillman et al. *Cancer Res.* 48:6097-6102 (1988) for using an acid-labile linker in a similar fashion to prepare conjugates of daunorubicin with an anti-T cell antibody; Trouet et al., *Proc. Natl. Acad. Sci.* 79:626-629 (1982) for linking daunorubicin to an antibody via a peptide spacer arm.

An antibody (or polypeptide) of this invention may be conjugated (linked) to a radioactive molecule by any method known to the art. For a discussion of methods for radiolabeling antibody see "Cancer Therapy with Monoclonal AntibodiesT", D. M. Goldenberg ed. (CRC Press, Boca Raton, 1995).

Alternatively, an antibody can be conjugated to a second antibody to form an antibody heteroconjugate as described by Segal in U.S. Pat. No. 4,676,980. The formation of cross-linked antibodies can target the immune system to specific types of cells, for example, cancer or diseased cells expressing RAAG10.

This invention also provides methods of delaying development of metastasis in an individual with cancer (including, but not limited to, prostate, lung, breast, ovarian, pancreatic, or colon cancer) using an anti-RAAG10 antibody or other embodiments that bind to RAAG10 linked to a chemotherapeutic agent. In some embodiments, the antibody is a humanized or chimeric form of a non-human anti-RAAG10 antibody.

In yet another embodiment, the antibody can be employed as adjuvant therapy at the time of the surgical removal of a cancer expressing the antigen in order to delay the development of metastasis. The antibody or antibody associated with a chemotherapeutic agent can also be administered before surgery (neoadjuvant therapy) in an individual with a tumor expressing the antigen in order to decrease the size of the tumor and thus enable or simplify surgery, spare tissue during surgery, and/or decrease the resulting disfigurement.

In yet another embodiment, any of the RAAG10 binding embodiments described herein can bind to RAAG10-expressing cancerous cells and induces an active immune response against the cancerous cells expressing RAAG10. In some cases, the active immune response can cause the death of the cancerous cells (e.g., antibody binding to cancer cells inducing apoptotic cell death), or inhibit the growth (e.g., block cells cycle progression) of the cancerous cells. In other cases, any of the novel antibodies described herein can bind to cancerous cells and antibody dependent cellular cytotoxicity (ADCC) can eliminate cancerous cells to which anti-RAAG10 binds. Accordingly, the invention provides methods of stimulating an immune response comprising administering any of the compositions described herein.

In some cases, antibody binding can also activate both cellular and humoral immune responses and recruit more natural killer cells or increased production of cytokines (e.g., IL-2, IFN-γ, IL-12, TNF-α, TNF-β, etc.) that further activate an individual's immune system to destroy cancerous cells. In yet another embodiment, mKID2 can bind to cancerous cells, and macrophages or other phagocytic cell can opsonize the cancerous cells.

Various formulations of anti-RAAG10 antibodies or fragments thereof may be used for administration. In some embodiments, anti-RAAG10 antibodies or fragments thereof may be administered neat. In addition to the pharmacologically active agent, the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient. Excipients as well as formulations for parenteral and nonparenteral drug delivery are set forth in *Remington, The Science and Practice of Pharmacy* 20th Ed. Mack Publishing (2000).

Suitable formulations for oral administration include hard or soft gelatin capsules, pills, tablets, including coated tablets, elixirs, suspensions, syrups or inhalations and controlled release forms thereof.

Generally, these agents are formulated for administration by injection (e.g., intraperitoneally, intravenously, subcutaneously, intramuscularly, etc.), although other forms of administration (e.g., oral, mucosal, etc) can be also used. Accordingly, anti-RAAG10 antibodies are preferably combined with pharmaceutically acceptable vehicles such as saline, Ringer's solution, dextrose solution, and the like.

The particular dosage regimen, i.e., dose, timing and repetition, will depend on the particular individual and that individual's medical history. Generally, a dose of at least about 100 ug/kg body weight, more preferably at least about 250 ug/kg body weight, even more preferably at least about 750 ug/kg body weight, even more preferably at least about 3 mg/kg body weight, even more preferably at least about 5 mg/kg body weight, even more preferably at least about 10 mg/kg body weight is administered.

Empirical considerations, such as the half-life, generally will contribute to the determination of the dosage. Antibodies, which are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is based on reducing the number of cancerous cells, maintaining the reduction of cancerous cells, reducing the proliferation of cancerous cells, or delaying the development of metastasis. Alternatively, sustained continuous release formulations of anti-RAAG10 antibodies may be appropriate. Various formulations and devices for achieving sustained release are known in the an.

In one embodiment, dosages for anti-RAAG10 antibodies may be determined empirically in individuals who have been given one or more administration(s). Individuals are given incremental dosages of an anti-RAAG10 antibody. To assess efficacy of anti-RAAG10 antibodies, a marker of the specific cancer disease state can be followed. These include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer), a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of cancer, the stage of cancer, whether the cancer has begun to metastasize to other location in the individual, and the past and concurrent treatments being used.

Other formulations include suitable delivery forms known in the art including, but not limited to, carriers such as liposomes. See, for example, Mahato et al. (1997) *Pharm. Res.* 14:853-859. Liposomal preparations include, but are not limited to, cytofectins, multilamellar vesicles and unilamellar vesicles.

In some embodiments, more than one antibody may be present. The antibodies can be monoclonal or polyclonal. Such compositions may contain at least one, at least two, at least three, at least four, at least five different antibodies that are reactive against carcinomas, adenocarcinomas, sarcomas, or adenosarcomas. Anti-RAAG10 antibody can be admixed with one or more antibodies reactive against carcinomas, adenocarcinomas, sarcomas, or adenosarcomas in organs including but not limited to ovary, breast, lung, prostate, colon, kidney, skin, thyroid, bone, upper digestive tract, and pancreas. In one embodiment, a mixture of different anti-RAAG10 antibodies are used. A mixture of antibodies, as they are often denoted in the art, may be particularly useful in treating a broader range of population of individuals.

The following examples are provided to illustrate, but not to limit, the invention.

EXAMPLES

Example 1

Preparation of Human Fetal Bladder Cells and Human Pancreatic Cells (hPED) as Immunogens To prepare human fetal bladder cells for use as an immunogen, the following methods were used. Human fetal bladders of gestational age between 14 to 21 weeks were obtained from Advanced Bioscience Research at Alameda County, Calif. Bladders were procured and shipped to the lab in tissue culture medium on wet ice. Immediately upon arrival, the bladders were washed three times with 20 ml cool PBS. Under the dissection microscope, bladders were cleaned of extra tissues around bladder, and washed two more times with cool PBS. The bladders were minced into 1 mm cube with a razor blade in a 100 mm dry culture-dish. Ten ml Opti-MEM medium (GIBCO BRL Cat. No. 22600) was added. The tissue pieces were transferred into a 15 ml centrifuge tube by a 5 ml pipette, which was pre-coated with 5% BSA in PBS. The tissue pieces were then centrifuged at 1000-x g for 5 minutes. The pellet was resuspended in 6 ml Opti-MEM medium. The tissue was cultured in a 6 well-plate with 3 ml Opti-MEM medium per well, which contained following growth factors (final concentration in each milliliter medium); insulin 10 µg/ml, transferrin 10 µg/ml, vitamin E 5 µg/ml, aprotinin 25 µg/ml, progesterone 3 ng/ml, KGF 10 ng/ml, Heregulin 5 nM, gentamycin 100 µg/ml (added in the first two days cell culture). Under this condition epithelial cells emigrated to form epithelial cell colonies. Limited-growth of fibroblast cells were seen in the initial culture, but those cells were removed by brief trypsinization. Trypsin (GIBCO BRL Cat. No. 25300-054) at final concentration of 0.05% was added to get rid of the fibroblast cell three days before injection.

In other embodiments, the tissue source is a human progenitor cell line derived from human fetal tissue, expanded, and recombined with rat or mouse mesenchyme selected to promote differentiation and maturation of the progenitor cells to one or more mature human cell types to form a human/rodent tissue recombinant. For example, such tissue recombinants can be human pancreatic progenitor cells (hPED) isolated and grown as described in U.S. Pat. No. 6,436,704, human Mullerian progenitor cells isolated and grown as described in U.S. Pat. No. 6,416,999, human ovarian progenitor cells isolated and grown as described in WO 01/77303 or human bladder progenitor cells (hBLA) as described in pending patent application PCT/US03/04547, the teaching of all of which are specifically incorporated by reference herein.

To harvest the cells, the cells were rinsed once with calcium and magnesium free Hanks saline solution, incubated in 0.02% EDTA in Hanks saline solution at 37° C. for 15 minutes. The cells were detached from the culture surface by gentle tapping. The cell suspension was precipitated by centrifuge at 1000 rpm for 10 minutes. The supernatant was removed and cells were resuspended in serum free medium (Opti-MEM) containing appropriate non-denaturing adjuvant.

To prepare human pancreatic progenitor cells for use as an immunogen, the following methods were used. These methods are described in U.S. Pat. No. 6,436,704, referenced above. Fetal pancreas (gestational age 14-22 weeks) was mechanically pulled apart by microdissection under a stereo microscope prior to enzymatic dissociation. Enzyme treatment consisted of placing the partly dissociated tissue in 1 ml F12/DMEM medium containing 5-mg/ml collagenase-dispase, 20 µg/ml soybean trypsin inhibitor and 50 µg/ml DNAase for 15 minutes at 37 degrees Celsius.

Cell aggregates were layered on top of a 5% (by volume) BSA gradient and washed by centrifugation for 6 minutes at 900 rpm. Pelleted cells which were still in aggregate form were resuspended in growth medium consisting of CMRL 1066 nutrient medium containing the following factors:

| | |
|---|---|
| Insulin | 10 µg/ml |
| Transferrin | 10 µg/ml |
| Epidermal growth factor | 5 ng/ml |
| Ethanolamine | $10^{-6}$ M |
| Phosphoethanolamine | $10^{-6}$ M |
| Selenium | $2.5 \times 10^{-8}$ M |
| Triiodothyronine | $10^{-12}$ M |
| Progesterone | $10^{-9}$ M |
| Hydrocortisone | $10^{-9}$ M |
| Forskolin | 1 µM |
| Heregulin | 10 nM |
| Aprotinin | 25 µg/ml |
| Bovine pituitary extract | 75 µg/ml |
| Gentamycin | 100 µg/ml |

Resuspended cell aggregates were aliquoted into fibronectin-coated wells (6-12) of a 24-well dish and incubated at 37 degrees Celsius in a humidified 5% $CO_2$ incubator for 72 hours. After 72 hours, the epithelial cells formed suspended spherical structures and the mesenchymal or stromal cells were attached to the surface of the well. Cells were subcultured at a 1:2 split every 4 days in F12/DMEM (50:50) medium with 1.2 gm/L bicarbonate and 10 mM Hepes buffer supplemented with the hormones shown above and plated on fibronectin-coated plates (12-well, then 6-well, then 60 mm, then 100 mm plates as the population grows).

Several other cell types were used as immunogens in the practice of this invention, following the methods described above, to generate and discover the novel anti-RAAG10 monoclonal antibodies of this invention.

Example 2

Generation of Monoclonal Antibodies

Human fetal bladder (HFB) cells between 11 and 16 days of culture were used to generate monoclonal antibodies. Human pancreatic progenitor (hPED) cells were used for injection as an immunogen and screening for antibodies largely between passages 3 and 5. Approximately $10^6$ HFB or human pancreatic progenitor cells per mouse were injected into Balb/c mice via foot-pad, once a week. Non-denaturing adjuvants, (e.g., Ribi) were used. After 6 weeks of weekly injection, a drop of blood was drawn from the tail of each immunized animal to test the titer of antibodies against HFB using FACS analysis. When the titer reached at least 1:2000, the mice were sacrificed in a $CO_2$ chamber followed by cervical dislocation. Lymph nodes were harvested for hybridoma preparation.

Lymphocytes from mice with the highest titer were fused with the mouse myeloma line X63-Ag8.653 using 35% polyethylene glycol 4000. On day 10 following the fusion, the hybridoma supernatants were screened for the presence of HFB or human pancreatic progenitor cell specific monoclonal antibodies by fluorescence activated cell sorting (FACS). Conditioned medium from each hybridoma was incubated for 30 minutes with an aliquot of HFB cells or human pancreatic progenitor cells. After incubation, the cell samples were washed, resuspended in 0.1 ml diluent and incubated with 1 µg/ml of FITC conjugated F(ab')2 fragment of goat anti-mouse IgG for 30 min at 4° C. The cells were washed, resuspended in 0.5 ml FACS diluent and analyzed using a FACScan cell sorter (Becton Dickinson; San Jose, Calif.). Hybridoma clones were selected for further expansion, cloning, and characterization based on their binding to the surface of HFB cells or human pancreatic progenitor cells as assessed by FACS. One hundred hybridoma clones were found positive in this primary screen.

The positive hybridomas were further screened for their reaction to normal tissue sections. Hybridoma clones negative on kidney, lung, and skin tissue sections were collected. These hybridomas making the monoclonal antibodies designated anti-RAAG10 family antibodies were selected.

Example 3

Purification of Anti-RAAG10 Family Monoclonal Antibodies

Anti-RAAG10 family antibodies, the volume of supernatant was measured and an equal volume of binding buffer was added to the supernatant. The mixture was allowed to equilibrate to room temperature. The supernatant was clarified by passage through a 0.22 µm filter. The supernatant was loaded on to a protein-G column using the GradiFrac system. The column was washed with 5-10 column volumes of binding buffer. The monoclonal antibodies were eluted with the elution buffer and 2 ml fractions were collected. An $OD_{280}$ reading of the fractions were obtained and the fractions containing monoclonal antibodies were pooled. The eluted monoclonal antibody fractions were neutralized by adding 1/20 volume of 3M Tris. The sample was dialyzed in 1×PBS at 4° C. (with 3 buffer changes of at least 3 hours per change). The purified monoclonal antibodies were sterile filtered (0.2 uM) and stored at 2-8° C.

After purification of the anti-RAAG10 family monoclonal antibodies from the hybridoma supernatant, it was re-tested for binding to HFB cells or hPED. The cell samples were prepared as described above in Example 4 and incubated with the purified antibody at various concentrations After incubation the cells were washed, resuspended in 0.1 ml diluent and incubated with 1 µg of FITC conjugated F(ab')2 fragment of goat anti-mouse IgG for 30 min at 4° C. The cells were washed, resuspended in 0.5 ml FACS diluent and analyzed using a FACScan cell sorter (Becton Dickinson; San Jose, Calif.). A shift to the right on the FACScan histogram indicated that the purified antibody still bound to the HFB cells or hPED.

Four monoclonal antibodies were purified as referred to herein as BLA8, LUCA1, PA20, and SKIN2. The hybridomas producing these respective antibodies have ATCC Designation of PTA-4218. PTA-4217, PTA-4244 and PTA-4245, respectively. Subsequently five additional monoclonal antibodies were purified, referred to herein as LUCA1, GB8, KID1, KID13, and OVCA22.

Example 4

Identification and Characterization of Antigen to which Anti-RAAG10 Family Antibodies Bind Antibody BLA8:

To identify the antigen to which BLA8 was reactive, an immunoprecipitation experiment was performed. For immunoprecipitation, 10 ml of packed LnCap cells were lysed with 40 ml lysis buffer. The lysis buffer consisted of hanks balanced salt solution (HBSS+) fortified with 2% Triton X-100, protease inhibitor cocktail (1 tablet per 5 ml lysis buffer of complete mini EDTA free protease cocktail from Roche Molecular Biochemicals), 0.1% sodium azide, and 2 mM PMSF. The cell lysate was clarified at 24,000×g for 30 minutes at 4° C. before being passed over a column consisting of 2 mg/ml mouse IgG conjugated CNBr 6 MB sepharose beads, the lysate is now deemed pre-cleared. The pre-cleared LnCap lysate was then passed over a BLA8 conjugated CNBr sepharose 6 MB column. The BLA8 column was conjugated at 3 mg BLA8 per ml of swollen CNBr 6 MB sepharose beads. The beads (both mouse IgG and BLA8) were then washed three times with lysis buffer before elution with 0.1M glycine, pH 2.5. Eluates were collected at 1 column volume fractions and neutralized with a final concentration of 0.1M Tris, pH 8.0, resulting in a final pH of ~7.2. Neutralized fractions were then concentrated to 10% of fraction volume with microconcentrators (Centricon 10 from Millipore). 10% of the concentrated eluate was then resolved by SDS-PAGE and western blotting. At the same time, 30% of the eluate was further concentrated to a volume compatible for SDS-PAGE and resolved through Commassie staining.

By western blotting the alkylated BLA8 and mouse IgG eluate against BLA8, a triplet of heavily glycosylated proteins unique to the BLA8 eluate (>223 kDa, ~200 kDa, and 100 kDa) was observed, with the 100 kDa band being the most prominent. Because of the linearity of the three bands (i.e. 200 kDa is a doubling of 100 kDa, and the >223 kDa band may be a tripling of the 100 kDa band), it was hypothesized that the three bands consisted of a monomeric, dimeric, and trimeric form of the BLA8 antigen. The stacking effect of the purified antigen indicates that the antigen may well dimerized in the native state, but the concentration is artificially forcing the proteins to interact with each other at a higher frequency. By commassie staining, there was observed to be a BLA8 unique doublet at 100 kDa and ~200 kDa. A faint third band was observed >223 kDa. To confirm our hypothesis, both the 100 kDa and ~200 kDa bands were cut out and labeled LO (100 kDa) and HI (~200 kDa). These two bands are then submitted for mass spec analysis.

Similar methods were followed to identify and characterize the antigens to which monoclonal antibodies LUCA1, PA20 and SKIN2 bind, and similar results were obtained.

To determine the molecular weight of the target antigen for MAbs BLA8, LUCA1, PA20 and SKIN2 by Western blotting analyses, several commercially available human cancer cell lines were obtained from the American Type Culture Collection such as Colo 205, HPAF-II, LnCAP, Panc-1, SK-OV-3, SK-MES, SK-OV-3. These cell lines were grown in a 1:1 mixture of F12 medium (GibcoBRL, Cat. No. 21700-091) and DMEM medium (GibcoBRL, Cat. No. 12100-061) containing L-glutamine and 10% fetal bovine serum. The cells were grown to confluency in a 37°

C. incubator with 5% $CO_2$. Approximately thirty to fifty confluent $T_{175}$ flasks of each cell line were harvested using 10 mM EDTA in phosphate buffered saline. The harvested cells were centrifuged for 5 minutes at 1200 rpm in a Beckman GS-6KR tabletop centrifuge. The supernatants were discarded, and the cell pellets were resuspended in 0.5 mL of deionized water and 10 µL Protease Inhibitor Cocktail per $T_{175}$ flask (Sigma, Cat. No. P8340). The cell suspensions were frozen at −80° C., then thawed. This freeze/thaw cycle was repeated for a total of five times in order to disrupt the cell membranes.

The disrupted cell membranes were then collected by centrifugation in a Biofuge microfuge (Haereus) at maximum speed for 15 minutes at 4° C. The supernatants contain the cytoplasmic and nuclear proteins. Supernatants were removed and retained for further analysis. The pellets, containing the cell membrane fragments, were resuspended and solubilized in approximately 4 mL of Hank's Balanced Salt Solution (HBSS, GibcoBRL, Cat. No. 14175-079) containing 2% Empigen BB (Calbiochem, Cat. No. 324690) and 100 µL of the Protease Inhibitor Cocktail, pH 7.0. The soluble cell membrane proteins were incubated on a rotator at 4° C. overnight.

The cell membrane protein extracts were centrifuged in a Biofuge microfuge at maximum speed for 15 minutes at 4° C. in order to remove any insoluble cell debris. The supernatants contain the extracted cell membrane proteins. Supernatants were collected and stored at −80° C. until used for Western blotting analyses.

The cell membrane protein extracts were separated by electrophoresis using pre-cast 4-12% NuPAGE gels (Invitrogen, Cat. No. NP0322). The extracts were diluted 10-fold in LDS sample buffer (Invitrogen, Cat. No. NP007), and were heated to 70° C. for 10 minutes, then were centrifuged in a microcentrifuge and vortexed to mix. A total of 3.0 µL of protein extract per lane was loaded onto the gel. Pre-stained molecular weight standards (BioRad, Cat. No. 161-0372) were also included. Electrophoresis was then performed according to the manufacturer's instructions. After electrophoresis, the gels were transferred onto nitrocellulose membranes (Invitrogen, Cat. No. LC2000), also according to the manufacturer's instructions. Transferred proteins were bound to the membranes by heating the nitrocellulose in PBS in a microwave oven for three minutes at high power. The membranes were then incubated in blocking buffer for 30 minutes to reduce non-specific binding. Protein-G purified monoclonal antibodies were then used to probe the nitrocellulose membranes. MAbs BLA8 (lot 080-06), LUCA1 (lot 102-06), PA20 (lot 102-10) and SKIN2 (lot 083-95) were diluted to approximately 4 µg/mL in blocking buffer. The nitrocellulose membranes were incubated with 8 mL of the diluted MAbs for one hour at room temperature on a rocker. A Western Breeze western blotting kit (Invitrogen, Cat. No. WB7103) was used to develop the Western blots according to the manufacturer's instructions. A glycosylated protein band at an approximate molecular weight of 85-90 kD was observed for each of the monoclonal antibodies using the above methodology. The intensity and pattern of binding to the various cell membrane protein extracts was consistent between all the antibodies in this family.

Western blotting analyses were also performed using reduced cell membrane protein extracts and tissue section homogenates. Sections of frozen normal human breast, kidney, lung and skin were collected into Eppendorf tubes. The sections were washed with PBS, and the samples were centrifuged at 16,000 rpm in an Eppendorf microcentrifuge at 4° C. for 15 minutes. The tissue pellets were solubilized in 100 µL of 2% Empigen BB in HBSS containing 20 µL protease inhibitor cocktail using a Branson Sonifier 250 for 30 seconds on ice.

The tissue extracts were centrifuged at 16,000 rpm in an Eppendorf microcentrifuge at 4° C. for 15 minutes in order to remove any insoluble cell debris. The supernatants contain the extracted tissue proteins. Supernatants were collected and stored at −80° C. until used for Western blotting analyses.

The tissue extracts, selected cell membrane protein extracts and affinity-purified antigen for MAb BLA8 were separated by electrophoresis using pre-cast 4-12% NuPAGE gels. The extracts were diluted in LDS sample buffer (Invitrogen, Cat. No. NP007) containing the reducing agent DTT (invitrogen Cat. No. NP0004), and were heated to 70° C. for 10 minutes, then were centrifuged in a microcentrifuge and vortexed to mix. A total of 6.0 µL of tissue or protein extract or purified antigen per lane was loaded onto the gel. Pre-stained molecular weight standards (BioRad, Cat. No. 161-0372) were also included. Electrophoresis was then performed according to the manufacturer's instructions, including the addition of antioxidant (Invitrogen Cat. No. NP0005) to the running buffer. After electrophoresis, the gels were transferred onto nitrocellulose membranes (Invitrogen, Cat. No. LC2000), also according to the manufacturer's instructions. Transferred proteins were bound to the membranes by heating the nitrocellulose in PBS in a microwave oven for three minutes at high power. The membranes were then incubated in blocking buffer for 30 minutes to reduce non-specific binding. Protein-G purified monoclonal antibodies were then used to probe the nitrocellulose membranes. MAbs BLA8 (lot 080-06), LUCA1 (lot 102-06), PA20 (lot 102-10) and SKIN2 (lot 083-95) were diluted to approximately 4 µg/mL in blocking buffer. The nitrocellulose membranes were incubated with 8 mL of the diluted MAbs for one hour at room temperature on a rocker. A Western Breeze western blotting kit (Invitrogen, Cat. No. WB7103) was used to develop the Western blots according to the manufacturer's instructions. A glycosylated protein band at an approximate molecular weight of 85-90 kD was observed for each of the monoclonal antibodies using the above methodology. Although the intensity of the binding to the reduced protein band is less than when it is not reduced, the band was still recognized by the four MAbs. This effect is more apparent in the cell membrane protein extracts than in the purified BLA8 antigen, which shows strong binding for each of the MAbs. No antigen was observed in the normal tissue samples.

Murine IgG was used as a control for both the unreduced and reduced Western blots. The same concentration of murine IgG was used when the murine IgG were used as monoclonal antibody probes. These controls show that there are, in fact, immunoglobulin artifacts present as ~25 and 50 kD bands in the Western blots. These are due to the presence of light and heavy chains derived from endogenous IgG present in the tissue sections or as a consequence of the affinity-purification of the BLA8 antigen.

Example 5

Isolation of Antigen of Anti-RAAG10 Antibody for Mass Spectrometry

Purified antibody anti-RAAG10 was covalently coupled cyanogen bromide-activated (CNBr) Sepharose 4B resin (Amersham Pharmacia Biotech Cat. No. 17-0430-01)

according to the manufacturer's instructions at a concentration of 2 mg BLA8 mAb per ml swollen sepharose bead volume. Freshly grown LNCap cells were harvested from 30 confluent T-175 culture flasks. The cells were pelleted centrifugally, resuspended in lysis buffer (Hank's Balanced Salt Solution (HBSS+) containing 2% Triton X-100, protease inhibitors, and 0.1% sodium azide) at a ration of 500 µl lysis buffer per 1 T175 flask. The cells were removed by scraping with a cell scraper. The cell/lysis buffer suspension was vortexed to mix and then clarified by centrifugation at 24,000×g for 45 minutes at 4° C. The clarified lysate was removed and pre-cleared against mouse IgG conjugated CNBr sepharose for 2 hours at 4° C. The pre-cleared lysate was then passed over the BLA8 CNBr sepharose matrix. BLA8 beads were then extensively washed with the lysis buffer (at least 10 column volumes) before elution with 0.1M glycine, pH 2.5. The matrix was eluted with a total of 5 column volume of elution buffer. The eluate was collected in fractions of single column volumes. Each faction was independently concentrated on a centricon-10 concentrator (Millipore, #4206) until the volume reaches ~60 µl, 10% of the eluate was resolved by SDS-PAGE and analyzed by western blotting. The remaining 90% was loaded onto a single lane and resolved by SDS-PAGE and commassie staining. Three bands typical to glycoproteins were observed by commassie staining at and around 100, 200, and 250+ kDa range, the strongest band was the 100 kDa band, followed by the 200 kDa band, the 250 kDa+band was the faintest in staining. These bands corresponded with the bands observed by western blotting, and was theorized to represent the monomer (100 kDa), homo-dimer (200 kDa), and homo-trimer (250+kDa) forms of a single protein. The bands at 100 kDa and 200 kDa were excised and submitted for mass spectrophotometric analysis.

Example 6

MALDI Mass Spectrometry

The antigen to which anti-RAAG10 antibodies binds is isolated as described in Example 4 and 5 and subject to MALDI mass spectroscopy. Eluates of the immunoaffinity column are separated by SDS-PAGE, and the bands are excised and extracted. The gel slice is tryptically digested "in gel" (Gharahdaghi, F., Weinberg, C. R., Meagher, D. A., Imai, B. S., and Mische. S. M. (1999) Electrophoresis 20, 601-605). Extracted peptides are analyzed by matrix-assisted laser desorption/ionization time-of-flight mass spectrometry (MALDI-Tof) on a Kratos, AXIMA CFR. Peptide masses are determined within 100 ppm and a time ion gate with a curved field reflectron is employed for peptide isolation and fragmentation via post-source-decay (PSD). Searches are conducted with the Protein Prospector Programs (Clauser K. R., Baker P. R., and Burlingame A. L., Analytical Chemistry, Vol. 71, 14, 2871-(1999)) MSFit and MSTag.

Five major peptide peaks were identified, at masses of 1173.6016 (Peptide 1), 1601.7634 (Peptide 2), 1686.9179 (Peptide 3), and 1991.0310 (Peptide 4), and 2620.3834 (Peptide 5). Searches of human protein databases indicated that Peptides 2 and 3 could have been generated from a protein termed "b7 homolog 3" (NCBI Accession number 13376852). Post source decay analysis of select peptides confirmed the identity of these peptides as the correct sequence. A further screen on hypothetical protein sequences of EST (expressed sequence tag) databases identified an additional protein that contained all 5 peptide Peptides (with the identity confirmed by post source decay). This protein comes from a human EST and is designated as follows: 602309922F1 NIH_MGC_88 *Homo sapiens* cDNA clone IMAGE: 4401173 5'.

All five masses and PSD analysis matched the sequences in this hypothetical protein. Sequence comparisons of the DNA and derived protein from the EST and from the sequence of that of the B7 homolog 3 indicated that major parts of the sequences overlapped. The non-identical sequences began at the area in the amino terminus of the B7 homolog 3, shortly after the signal sequence. This indicates that the EST is actually from a cDNA clone of an alternative splice variant of the B7 homolog 3, with the coding region extending an unknown amount in the 5' direction. Since the deglycosylated purified antigen has a molecular weight of approximately 60,000 Daltons, (and that of the B7 homolog 3 has a molecular weight of approximately 30,000 Daltons), the protein data is consistent with the actual protein containing additional coding sequence in addition to that known for the B7 homolog 3.

Since one of the peptides (Peptide 4) is very homologous to a sequence within the B7 homolog 3 just prior to a hydrophobic area (the putative transmembrane domain), and without intent to be bound to any particular theory or mechanism, it may be that the RAAG10 antigen has arisen from a duplication of the B7 homolog 3 extracellular domains (consisting of two IgG-like domains), generating a putative protein consisting of 4 IgG-like domains, the transmembrane domain, and a cytoplasmic "tail".

Determination of the exact structure of the RAAG10 antigen will be determined using the existing sequence information for the EST and for the B7 homolog 3, using standard techniques to extend the cDNA sequence in the 5' direction until the start AUG codon is identified. Any of the cell lines described elsewhere in this document can be used as the source of cDNA libraries for this work.

Example 7

BLA8 Antigen Characterization

To identify the antigen to which BLA8 was reactive, an immunoprecipitation (Ippt) experiment was performed. For Ippt, 10 ml of packed LnCap cells were lysed with 40 ml lysis buffer. The lysis buffer consisted of Hanks balanced salt solution (HBSS+) fortified with 2% Triton X-100, protease inhibitor cocktail (1 tablet per 5 ml lysis buffer of complete mini EDTA free protease cocktail from Roche Molecular Biochemicals), 0.1% sodium azide, and 2 mM PMSF. The cell lysate was clarified at 24,000×g for 30 minutes at 4° C. before being passed over a column consisting of 2 mg/ml mouse IgG conjugated CNBr 6 MB sepharose beads, and the lysate was now deemed pre-cleared. The pre-cleared LnCap lysate was then passed over a BLA8 conjugated CNBr sepharose 6 MB column. The BLA8 column was conjugated at 3 mg BLA8 per ml of swollen CNBr 6 MB sepharose beads. The beads (both mouse IgG and BLA8) were then washed three times with lysis buffer before elution with 0.1M glycine, pH 2.5. Eluates were collected at 1 column volume fractions and neutralized with a final concentration of 0.1M Tris, pH 8.0, resulting in a final pH of ~7.2. Neutralized fractions were then concentrated to 10% of fraction volume with microconcentrators (Centricon 10 from Millipore). 10% of the concentrated eluate was then resolved by SDS-PAGE and western blotting. At the same time, 30% of the eluate was further concentrated to a volume compatible for SDS-PAGE and resolved through commassie staining.

By western blotting the alkylated BLA8 and mouse IgG eluate against BLA8, a triplet of heavily glycosylated proteins unique to the BLA8 eluate (>223 kDa, ~200 kDa, and 100 kDa) was observed, with the 100 kDa band being the most prominent. Because of the linearity of the three bands (ie, 200 kDa is a doubling of 100 kDa, and the >223 kDa band may be a tripling of the 100 kDa band), it was hypothesized that the three bands consisted of a monomeric, dimeric, and trimeric form of the BLA8 antigen. The stacking effect of the purified antigen indicates that the antigen may well dimerized in the native state, but the concentration is artificially forcing the proteins to interact with each other at a higher frequency. By commassie staining, there was observed to be a BLA8 unique doublet at 100 kDa and ~200 kDa. A faint third band was observed >223 kDa. To confirm our hypothesis, both the 100 kDa and ~200 kDa bands were cut out and labeled LO) (100 kDa) and ill (~200 kDa). These two bands are then submitted for mass spec analysis.

By mass spec analysis, the two bands (HI and LO) yield the identical peptic peaks, indicating that the two bands consisted of the identical antigen, confirming our hypothesis that the bands observed by western blotting and SDS-PAGE were indeed polymers of the antigen, which has a glycosylated molecular weight of ~100 kDa. Also by mass spec, an identification was made on the BLA8 antigen. The peptide sequences for the BLA8 antigen was a match to two banked sequences, the first of which is a recently identified protein B7-H3, the second being an EST sequence which shares >90% homology with the B7-H3 extracellular domain sequence but is coding for a much larger sequence. We have discovered that BLA8 is binding to a novel antigen that is similar to B7-H3. We term this antigen B7-H3L.

Example 8

Antibodies LUCA1, SKIN2, PA20 and BLA8 are all Directed to the Same Antigen

To confirm the western blotting results that demonstrate that the antibodies LUCA1, SKIN2, PA20 and BLA8 all seem to be blotting to the same antigen, a solid phase plate ELSA was performed using purified BLA8 antigen from LnCap cells. The purified antigen was bound to NUNC maxisorb plates (VWR) at a 1:25 dilution (50 µl per well) in hank's balanced salt solution (HBSS+) for 2 hours at room temperature. The bound plate was then blocked for 30 minutes with 200 µl per well of HBSS+ containing 1% BSA. After blocking, LUCA1, SKIN2, PA20, and BLA8 (all at 0.5 µg/well, diluted in the blocking buffer) were added to the maxisorb plate and allowed to interact for 1 hour at room temperature. Mouse IgG and an irrelevant antibody that is reactive against LnCap cells were used, at the same concentration per well, as a negative control. The plates were washed thoroughly with HBSS+. The secondary antibody, horse radish peroxidase (HRP) conjugated donkey antimouse IgG (heavy and light chain specific) used at 0.04 µg/well, was then added to the wells and allowed to incubate for 30 minutes at room temperature. The plates were thoroughly washed with HBSS+ and then exposed to TMB substrate for an HRP based color change reaction. The reaction was stopped by the addition (1:1 versus the substrate) of 1M Phosphoric acid. The reactions were then read at O.D. 450. By this ELISA. LUCA1, SKIN2, PA20, and BLA8 all reacted strongly against the BLA8 antigen (at least a 2 fold O.D. 450 increase over the negative controls), while the negative controls showed little to no reactivity.

At the same time, a live cell ELISA was conducted using the four antibodies. It was discovered that the four antibodies all exhibited the same cell reactivities. Furthermore, LUCA1, PA20, SKIN2 and BLA8 were used to western blot against BLA8 purified antigen. All four antibodies reacted strongly to the BLA8 purified antigen.

From the two experiments performed, it was concluded that the antibodies LUCA1, PA20, SKIN2 and BLA8 all react to the same antigen.

Example 9

BLA8 Family and Epitope Competition

Because we had generated multiple antibodies to a single antigen, experiments were undertaken to determine if there were epitopic differences between four of the antibodies in the BLA8 family of mAbs (LUCA1, PA20, SKIN2, and BLA8). Due to quantitative limitations, only LUCA1, PA20, and BLA8 were biotinylated. For the biotinylation, 250 µg of each antibody, at a concentration of 2 mg/ml, were incubated with sulfo-NHS-LC-biotin, at a ratio of 200 µg of biotin/mg of antibody, in PBS for 2 hours at room temperature. The biotinylation was quenched by the addition of 1M Tris, pH 8.0 to a final concentration of 100 mM. The quenching reaction was allowed to incubate for a further 20 minutes at room temperature. The biotinylated antibody was then buffer exchanged into PBS.

BLA8 purified antigen was immobilized on NUNC maxisorb plates via a two hour incubation, at a concentration of 2 µl per well at a 1:25 dilution in hank's balanced salt solution (HBSS+). Coated plate was then blocked for 30 minutes at room temperature in HBSS+ containing 1% BSA. The blocking buffer was then removed from the plate, and the competitor antibody, non-biotinylated LUCA1, PA20, SKIN2, or BLA8, at a titration starting from 2 µg/well to 3.8 ng/well (50 ul/well) diluted in blocking buffer, was added to the wells for 30 minutes at room temperature. After the 30 minute incubation, the biotinylated antibody (LUCA1, PA20, or BLA8) was introduced to the competitor antibody containing wells at 50 µl/well. The biotinylated antibodies were added at a concentration of 500 ng/ml. The cocktail of competitor antibody and biotinylated antibody was allowed to incubate for a further 1 hour at room temperature. The plate was then thoroughly washed in HBSS+. Horseradish peroxidase (HRP) conjugated streptavidin, diluted in HBSS+, was then allowed to incubate for 30 minutes at room temp at 50 ul/well. The plate was further washed with HBSS+ and incubated with TMB substrate for HRP based color development. The reaction was stopped by the addition of 1M phosphoric acid. The plate was then read at O.D. 450.

From the competition assay, it was realized that PA20 and SKIN2 cross-competed, indicating that they share the same epitope, LUCA1 and BLA8, meanwhile, were competed only by themselves, indicating that they bound to distinct epitopes. Thus, in the BLAB family of antibodies, PA20, KID1 and SKIN2 bind an epitope we refer to as epitope A; LUCA1, KID13, and GB8 bind to the epitope we refer to as epitope B; and BLA8 binds to the epitope we refer to as epitope C.

Example 10

Cloning of RAAG10

Cloning of B7H3 Full-Length Complementary DNA

A human ovarian cancer cell SKOV3 cDNA library constructed in Gateway™ pCMV*SPORT6 vector (Invitrogen, Carlsbad, Calif.) was transfected into Chinese Hamster Ovary (CHO) cells using standard protocol. Transfectants expressing BLA8 antigen on the cell surface were enriched by "panning" two times on BLA8 antibody. After enrichment, cells were lysed to release DNA. The crude lysate was used as template for the cloning of B7H3 by polymerase chain reaction (PCR). Briefly, a pair of B7H3-specific primers (sense: 5'-AGCCGCCTCACAGGAAGATGCT-3' (SEQ ID NO:1), and antisense: 5'-CCCTGGTCCTCATGGTCA-GGCTAT-3'(SEQ ID NO:2)) were designed to flank the open reading frame (ORF) of B7H3 based on the EST sequences available in the GeneBank. PCR was performed by combining 1.5 µl cell lysate with 50 µmol each of B7H3-specific primers, nuclease-free $H_2O$, 1×PCR buffer. 200 µM each of dNTPs, and 2.5 U Platinum High-Fidelity Taq DNA polymerase (Invitrogen, Carlsbad, Calif.). The reaction mixture was incubated at 94° C. for 2 min, followed by 28 cycles of template denaturation at 94° C. for 10 sec and primer annealing/extension at 68° C. for 3 min. and a final extension at 68° C. for 10 min. An aliquot of the PCR product was resolved onto a 1.2% agarose gel and visualized by ethidium bromide staining. A predominant band at about 1.6 kb was identified, gel-purified and cloned into pTargeT™ mammalian expression vector (Promega, Madison, Wis.). The transformants were characterized by restriction fragment analysis using HindII, and the orientation of cDNA insert was determined by PCR. Clones with similar restriction patterns and correct orientation were selected for nucleotide sequencing. A 1605 bp ORF was discovered from seven of these clones, and all of them overlapped with B7H3 EST sequences available in the GeneBank. The authenticity of these cDNA clones were further confirmed by expressing them in CHO cells followed by staining with BLA8 antibody.

Construction and Characterization of B7H3 Mutants.

To determine which domain(s) of B7H3 was responsible for the binding of each BLA8 antibody family member, a series of B7H3 mutants were constructed, expressed in CHO cells and characterized by various methods. Briefly, a pTargeT/B7H3 eDNA clone with the most intense staining by BLA8 antibody was selected and subjected to digestion with different combinations of restriction enzymes that either flanked (BamHI and NotI) or located within (Eco47III); the B7H3 cDNA. After ligations, a series of mutants were created as summarized in Table 1. The authenticity of each mutant was checked by PCR and digestion with HindIII restriction enzyme. At least three clones of each mutant were transfected into CHO cells using standard protocol. Those B7H3 mutants-transfected CHO cells were then selected on 1 mg/ml G418 for 2 wk. Various methods were employed to assay the B7H3 content in different compartments of the cell: 1) Immunohistochemistry (IHC) was used for the localization of immunoreactive B71H3 on the surface or inside the transfectants; 2) Reverse-transcription polymerase chain reaction (RT-PCR) was used for the detection of mRNA expression in the transfectants; 3) Sandwich ELISA was used for the detection of secretory B7H3 in the culture supernatant. The results obtained for each method were from at least three independent experiments.

Immunohistochemical Staining of B7H3 Mutants-Transfected CHO Cells.

The presence of immunoreactive B7H3 in the transfectants was revealed by IHC. To determine whether B7H3 were expressed on the surface of CHO cells, live-cell IHC was performed. Briefly, cells were incubated with 10 µg/ml BLA8 antibody family (BLA8, LUCA1 or PA20) at 37° C. for 1 h. Cells were washed three times in serum-free Ham's F12 nutrient mixture and Dulbecco's modified Eagle's medium (F12/DMEM, 1:1, v/v), fixed in ice-cold 100% ethanol for 15 min and then air-dried completely. The endogenous peroxidase activity was quenched by incubating cells with ice-cold 2% $H_2O$/PBS for 15 min. After rinsing with PBS, cells were blocked with 5% normal Goat serum/PBS for 1 h and then incubated with 2 µg/ml of peroxidase-conjugated AffiniPure F(ab'), fragment Goat anti-Mouse IgG+IgM (H+L) (Jackson Immunoresearch Labs, West Grove, Pa.) in blocking buffer for 1 h. After washings, immunoreactive B7H3 on the cell surface was visualized by incubating cells with Sodium acetate buffer (pH 5.0) containing 3,3'-Diaminobenzidine (DAB) and $H_2O_2$. For the detection of immunoreactive B7H3 within CHO cells, fixed-cell IHC was performed in a similar procedure as described above. Cells were first fixed in ice-cold 100% ethanol and air-dried completely. After quenching of endogenous peroxidase activity, cells were washed, blocked, and then incubated with 10 µg/ml BLA8 antibody family at 37° C. for 1 h. After washings, cells were incubated with the same peroxidase-conjugated antibody. Staining signal was developed after washings. Negative control was obtained by staining Tris-buffer transfected CHO cells with BLA8 antibody family. The staining was evaluated under an inverted microscope, and the results were summarized in Table 3 under IHC columns. Results were graded as '+' for positive staining, '+/−' for weakly positive staining or '−' for negative staining.

Detection of B7H3 mRNA Expression by RT-PCR.

RT-PCR was performed to determine whether B7H3 mRNA was indeed expressed in the transfectants. Total RNA was isolated from B7H3 mutants-transfected CHO cells by TRIzol reagent (Invitrogen, Carlsbad, Calif.) according to manufacturer's instructions. The concentration of RNA was quantified by absorbance at 260 nm. Approximately 2-3 µg of total RNA was reverse-transcribed with 0.5 µg oligo-dT$_{15}$ using Superscript II RNase H⁻ reverse transcription system (Invitrogen, Carlsbad, Calif.) according to manufacturer's protocol. PCR was performed by combining 1 µl reverse-transcription product with 50 µmol each of B7H3 primers (for details, please see Table 2), nuclease-free $H_2O$, 1×PCR buffer, 200 µM each of dNTPs, and 2.5 U Platinum Taq DNA polymerase (Invitrogen, Carlsbad, Calif.) in a similar cycling condition as described above. The resultant PCR product was resolved onto a 1.2% agarose gel and visualized by ethidium bromide staining. Results were summarized in Table 3 under RT-PCR column and graded '+' for mutants with the correct amplicon detected or '−' for no amplicon detected.

Detection of Immunoreactive B7H3 in the Culture Supernatant by ELISA.

To explore the possibility that whether some of the B7H3 was secreted instead of anchoring onto the cell surface, a sandwich ELISA was developed to assay the content of immunoreactive B7H3 in the culture supernatant. Briefly, a 96-well ELISA plate was coated with 4 µg/ml BLA8 antibody in Carbonate buffer (pH 9.0) at 4° C. overnight. The plate was washed with 0.05% Tween-20/PBS and blocked with 3% BSA/PBS for 1 h. Duplicates of culture supernatants (4 times 10-fold dilution starting from neat to 1/1000) and BLA8 antigen standard (8 times 2-fold dilution starting from 16 µg/ml to 125 ng/ml) were prepared in PBS containing 3% BSA and 0.05% Tween-20, and they were allowed to incubate for 1 h. After washings, the plate was incubated with 4 µg/ml biotinylated LUCA1 antibody in 3% BSA/PBS for 1 h. The plate was washed and incubated with Vectastain Elite ABC reagent (Vector Labs, Burlingame, Calif.) for another hour. After washings, the bound B7H3 was visualized by color development in Citrate-Phosphate buffer containing o-Phenylenediamine and $H_2O_2$. Desired color intensity was obtained by addition of 2.5N $H_2SO_4$. Absorbance at 490 nm was determined in a Molecular Devices Emax ELISA plate reader (Molecular Devices, Sunnyvale, Calif.) interfaced with SOFTmax Pro software (Molecular Devices. Sunnyvale. Calif.). Blanks were obtained by using supernatant of Tris buffer-transfected CHO cells. Results were summarized in Table 3 under ELISA column, and graded as '+' when absorbance reading was greater than the blanks or '−' when absorbance reading was equal or less than the blanks.

TABLE 1

Mutagenesis of B7H3 by restriction enzymes

| Mutant name | Restriction enzyme(s) | Amino acid residues with respect to full-length B7H3 |
|---|---|---|
| Full-length B7H3 | None | 1-534 |
| ΔC | Eco47III | Δ132-349 |
| C | Eco47III | 132-349 |
| Δ5' | BamHI & Eco47III | 350-534 |
| Δ5's | BamHI & Eco47III | 132-534 |
| Δ3' | Eco47III & NotI | 1-131 |
| Δ3's | Eco47III & NotI | 1-349 |

TABLE 2

Primers used in the detection of B7H3 mRNA transcript by RT-PCR

| Transfectant | Primers used | Approximate amplicon size. |
|---|---|---|
| Full-length B7H3 | sense: 5'-AGCCGCCTCACAGGAAGATGCT-3' (SEQ ID NO: 1)<br>antisense: 5'-AGCGGCCACCTGCAGGCTGACGGCA-3' (SEQ ID NO: 3) | 440 bp & 1.1 kb |
| ΔC | sense: 5'-AGCCGCCTCACAGGAAGATGCT-3' (SEQ ID NO: 1)<br>antisense: 5'-GGGGAATGTCATAGGCTGCCCTGTGAT-3' (SEQ ID NO: 4) | 760 bp |
| C | sense: 5'-CCCTACTCGAAGCCCAGCATGACCCT-3' (SEQ ID NO: 5)<br>antisense: 5'-CACGGCTCCTGTGGGGCTTCTCT-3' (SEQ ID NO: 6) | 330 bp |
| Δ5' | sense: 5'-CCAGAGGCCCTGTGGGTGACCGT-3' (SEQ ID NO:7)<br>antisense: 5'-CCCTGGTCCTCATGGTCAGGCTAT-3' (SEQ ID NO: 2) | 220 bp |
| Δ5's | sense: 5'-CCAGAGGCCCTGTGGGTGACCGT-3' (SEQ ID NO: 7)<br>antisense: 5'-CCCTGGTCCTCATGGTCAGGCTAT-3' (SEQ ID NO: 2) | 220 bp |
| Δ3' | sense: 5'-AGCCGCCTCACAGGAAGATGCT-3' (SEQ ID NO: 1)<br>antisense: 5'-CAGGGCTCCTGTGAGGCAGAACCA-3' (SEQ ID NO: 8) | 110 bp |
| Δ3's | sense: 5'-AGCCGCCTCACAGGAAGATGCT-3' (SEQ ID NO: 1)<br>antisense: 5'-CACGGCTCCTGTGGGGCTTCTCT-3' (SEQ ID NO: 6) | 770 bp |

TABLE 3

Characterization of B7H3 mutants by various methods

| Transfectant | BLA8 IHC | LUCA1 IHC | PA20 IHC | RT-PCR | ELISA |
|---|---|---|---|---|---|
| Full-length B7H3 (1-534 aa) | + | + | + | + | − |
| Tris buffer-transfected CHO | − | − | − | − | − |
| ΔC (Δ132-349 aa) | + | + | − | + | − |
| C (132-349 aa) | − | − | − | + | − |
| Δ5' (350-534 aa) | − | − | − | + | − |
| Δ5's (132-534 aa) | − | − | − | + | − |
| Δ3' (1-131 aa) | − | − | − | + | − |
| Δ3's (1-349 aa) | +/− | +/− | +/− | + | +[1] |

[1]The concentration of immunoreactive B7H3 in the supernatant of 'Mutant Δ3's' was approximately 2.148 ± 0.48 µg/ml.

Figure 2:
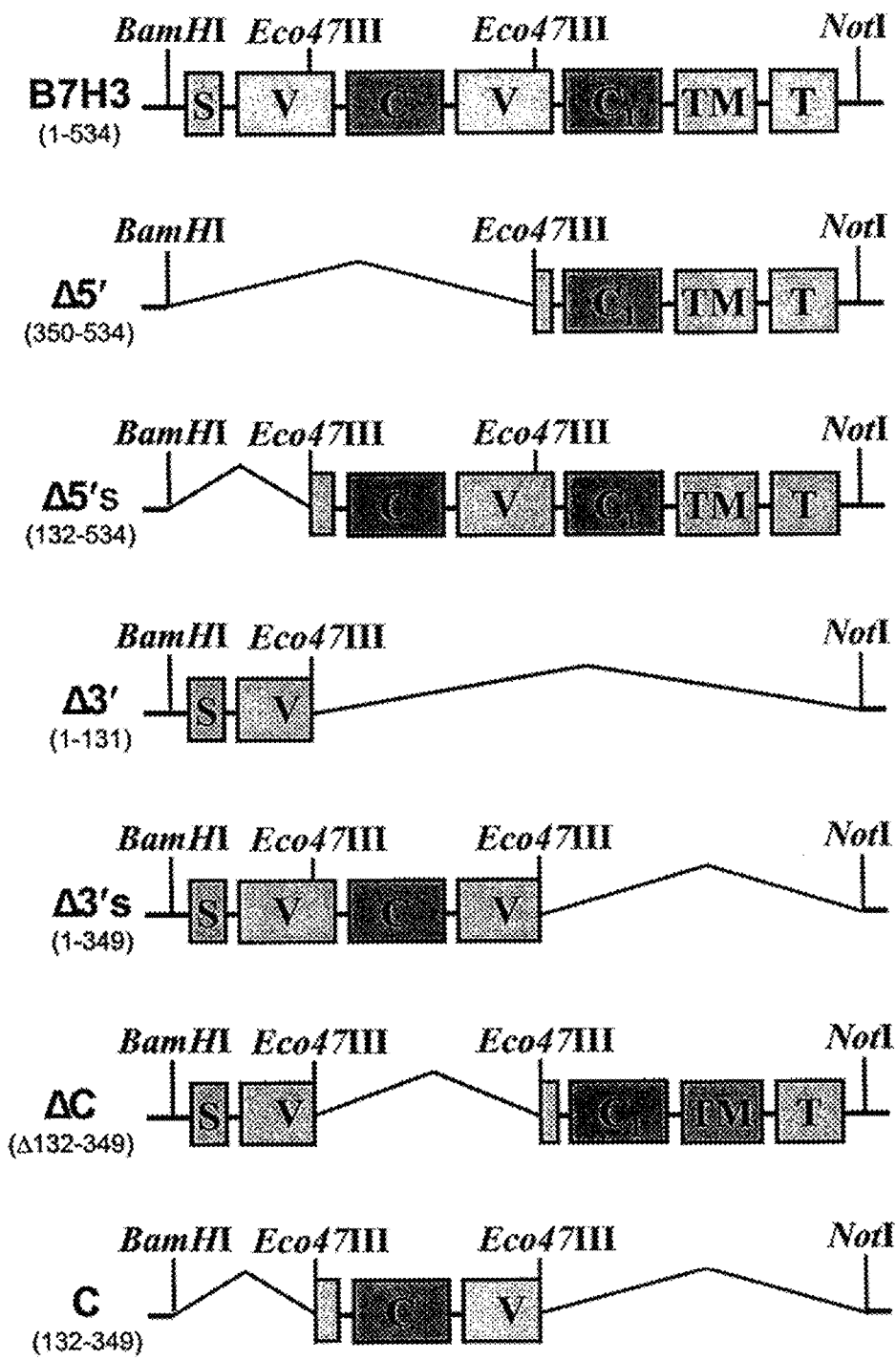
FIG. 2 shows a diagrammatic representation of B7H3 and its mutants.

A diagrammatic representation of B7H3 and its mutants is shown in FIG. 2.

Example 11

Immunohistochemistry for Binding of Anti-RAAG10 Family Antibodies to Tissues with Tumor Frozen tissue samples were embedded in OCT compound and quick-frozen in isopentane with dry ice. Cryosections were cut with a Leica 3050 CM mictrotome at thickness of 5 µm and thaw-mounted on glass slides. The sections were fixed with ethanol at −20° C. and allowed to air dry overnight at room temperature. The fixed sections were stored at −80° C. until use. For immunohistochemistry, the tissue sections were retrieved and first incubated in blocking buffer (PBS, 5% normal goat serum) for 30 minutes at room temperature, and then incubated with the anti-RAAG10 antibody and control monoclonal antibodies diluted in blocking buffer (5 µg/ml) for overnight. The sections were then washed three times with the blocking buffer. The bound monoclonal antibodies were detected with a goat anti-mouse IgG+IgM (H+L) F(ab')2-peroxidase conjugates and the peroxidase substrate diaminobenzidine (1 mg/ml, Sigma cat. No. D 5637) in 0.1 M sodium acetate buffer pH 5.05 and 0.003% hydrogen peroxide (Sigma cat. No. H1009). The stained slides were counter-stained with hematoxylin and examined under Nikon microscope.

In some cases, paraffin embedded formaldehyde-fixed tissues were used for immunohistochemistry after appropriate antigen retrieval methods were employee. One such antigen retrieval method is described in Mangham and Isaacson, *Histopathology* 35:129-33 (1999). Other methods of antigen retrieval and/or detection may be used by one skilled in the art. Results from similar experiments performed using frozen tissues or, where appropriate, fixed tissue with antigen retrieval and polyMICA detection were performed. The binding of anti-RAAG10 antibody to a variety of normal and cancer tissues was assessed. In all cases, antibody binding in control fixed tissues was correlated with that of frozen tissues. The results from frozen tissues were only used if the two did not match in the controls. For convenience. Table 4 shows the combined results of the staining of 5 major types of tumors with anti-RAAG10 antibody using frozen tumor tissues from 5 different sources. For each tumor type, the numbers of tumors testing positive for the antigen of anti-RAAG10 antibody, i.e., RAAG10, and the total number of such tumors tested is shown (+/total). The percentage of tumors binding anti-RAAG10 antibody is also indicated.

TABLE 4

Summary of the incidence of the anti-RAAG10 antibody binding to RAAG10 on major tumor types

| Colon | 3/6 |
|---|---|
| Lung | 6/6 |
| Breast | 2/2 |

TABLE 4-continued

Summary of the incidence of the anti-RAAG10 antibody binding to RAAG10 on major tumor types

| Prostate | 3/4 |
|---|---|
| Sarcoma | 1/1 |
| Total | 78.94% (15/19) |

Table 5 shows the combined results of the staining of 5 metastatic tumor types with anti-RAAG10 antibody using either fixed or frozen tumor tissues. For each tumor type, the numbers of tumors testing positive for the antigen of anti-RAAG10 antibody and the total number of such tumors tested is shown (+/total). The percentage of tumors binding anti-RAAG10 antibody is also indicated. As shown in Table 5, anti-RAAG10 antibody bound to about 94% of the metastatic tumor types tested.

TABLE 5

Summary of the incidence of the anti-RAAG10 antibody binding to RAAG10 On metastatic tumor types

| Breast metastasis | 9/9 |
|---|---|
| Metastatic Bronchial Carcinoma | 0/1 |
| Renal metastasis | 5/5 |
| Thyroid metastasis | 1/1 |
| Metatstatic Clear Cell Carcinoma | 1/1 |
| Total | 94.1% (16/17) |

Example 12

Immunocytochemistry Result from CellArray™

Monoclonal antibody anti-RAAG10 was used to test reactivity with various cell lines from different types of tissues. Cells from different established cell lines were removed from the growth surface without using proteases, packed and embedded in OCT compound. The cells were frozen and sectioned, then stained using a standard IHC protocol. The CellArray™ technology is described in WO 01/43869. The results were scored as '+' for weak positive staining, '++' for moderate positive staining, '+++' for strong positive staining and '−' for negative staining. Results from the CellArray binding experiments showing anti-RAAG10 antibody binding to various cell lines (including cancer cell lines) are summarized in Table 6.

TABLE 6

| Binding of Antibodies to Cell Lines | | | | | | | |
|---|---|---|---|---|---|---|---|
| Cell Name | ATCC# | Organ | Cell Type | BLA8 | LUCA1 | PA20 | SKIN2 |
| HMEC | CC-2551* | Breast | Human mammary epithelial | +++ | + | + | + |
| WI-38 | CCL-75 | Lung | Human fetal lung fibroblasts | +++ | fc+ | ++ | fc+ |
| RL-65 | CRL-10354 | Lung | Rat Clara Cell | − | − | − | − |
| COS7 | CRL-1651 | Kidney | African green monkey | +++ | nc | + | fc+ |
| SK-BR-3 | HTB-30 | Breast | Adenocarcinoma | + | nc | + | +/− |
| BT-474 | HTB-20 | Breast | Mammary gland, breast, ductal carcinoma | +++ | +++ | +++ | +++ |
| MCF7 | HTB-22 | Breast | Adenocarcinoma | +++ | +++ | +++ | +++ |
| HT29 | HTB-38 | Colon | Colorectal adenocarcinoma | +++ | + | ++ | ++ |
| SW480 | CCL-228 | Colon | Colorectal adenocarcinoma | ++ | +/− | +/− | +/− |
| ES-2 | CRL-1978 | | | ++ | + | ++ | + |
| SK-OV-3 | HTB-77 | Ovary | Adenocarcinoma | +++ | +++ | +++ | ++ |

TABLE 6-continued

Binding of Antibodies to Cell Lines

| Cell Name | ATCC# | Organ | Cell Type | BLA8 | LUCA1 | PA20 | SKIN2 |
|---|---|---|---|---|---|---|---|
| 9926 | RAVEN | Pancreas | Pancreatic cancer line developed at Raven | + | + | + | +/− |
| PANC-1 | CRL-1469 | Pancreas | Ductal epithelioid carcinoma | ++ | +/++ | + | + |
| AsPC-1 | CRL-1682 | Pancreas | Adenocarcinoma | ++ | + | ++ | ++ |
| Capan-1 | HTB-79 | Pancreas | Adenocarcinoma | ++ | +/− | + | + |
| 293 | CRL-1573 | Kidney | | +++ | ++ | +++ | +++ |
| CFPAC-1 | CRL-1918 | Pancreas | Pancreas ductal adenocarcinoma, cystic fibrosis | +++ | ++ | ++ | +++ |
| HPAF-II | CRL-1997 | Pancreas | Adenocarcinoma | ++ | +/− | + | + |
| Hs 700T | HTB-147 | Metastasis to the pelvis | Adenocarcinoma | +++ | +++ | +++ | +++ |
| Hs 766T | HTB-134 | Pancreas | Carcinoma | ++ | + | + | + |
| 786-O | CRL-1932 | Kidney | Renal cell adenocarcinoma | +++ | +++ | +++ | +++ |
| Caki-2 | HTB-47 | Kidney | Clear cell carcinoma | +++ | +++ | +++ | +++ |
| A498 | CRL-7908 | Kidney | Carcinoma | +++ | ++ | +++ | +++ |
| BHK-21 | CCL-10 | Kidney | Hamster syrian golden Normal Kidney | − | − | − | − |
| LNCaP | CRL-1740 | Prostate | Carcinoma | +++ | +++ | +++ | +++ |
| PC3 | CRL-1435 | Prostate | Adenocarcinoma | ++ | + | +/− | +/− |
| 22RV1 | CRL-2505 | Prostate | Carcinoma | +++ | + | ++ | +++ |
| DU145 | HTB-81 | Prostate | Carcinoma | +++ | ++/+++ | +++ | +++ |
| A549 | CCL-185 | Lung | Carcinoma | + | + | +/− | +/− |
| Ca130 | RAVEN | Lung | Proprietary Raven lung cancer line | ++ | ++ | ++ | ++ |
| SK-MES-1 | HTB-58 | Lung | Squamous cell carcinoma | +++ | +++ | +++ | +++ |
| Calu 3 | HTB-55 | Lung | Adenocarcinoma | +++ | ++ | +++ | ++ |

MAbs concentration = 5 μg/ml, Standard Protocol
*CC-2551 -Biowhittaker

Example 13

Binding of Anti-RAAG10 Antibody to Tumor and Normal Tissues

Normal tissues and tumor tissues obtained by surgical resection were frozen and mounted. Cryosections were cut with a Leica 3050 CM mictrotome at thickness of 5 μm and thaw-mounted on vectabound-coated slides. The sections were fixed with ethanol at −20° C. and allowed to air-dry overnight at room temperature. Primary antibody anti-RAAG10 was used at a dilution of 1 to 100 (final concentration of 1 ug/ml). The tissue sections were retrieved and first incubated in blocking buffer (PBS, 5% normal goat serum) for 30 minutes at room temperature, and then incubated with the anti-RAAG10 antibody and control monoclonal antibodies diluted in blocking buffer (5 μg/ml) for overnight. The sections were then washed three times with the blocking buffer. The bound monoclonal antibodies were detected with a goat anti-mouse IgG+IgM (H+L) F(ab')$_2$-peroxidase conjugates and the peroxidase substrate diaminobenzidine (1 mg/ml, Sigma cat. No. D 5637) in 0.1 M sodium acetate buffer pH 5.05 and 0.003% hydrogen peroxide (Sigma cat. No. H1009). The stained slides were counter-stained with hematoxylin and examined under Nikon microscopePolyMICA™ Detection kit was used to determine binding of anti-RAAG10 antibody.

The results were scored as '+' for weak positive staining. '++' for moderate positive staining, '+++' for strong positive staining and '−' for negative staining. Table 7 shows the binding of anti-RAAG10 antibody to tumor tissue samples. The results of staining of normal tissues with anti-RAAG10 antibody are shown in Table 8.

The results using a relatively more sensitive protocol (ABC or Dako Envision) showed staining in adrenal, uterus, skin, lung, kidney, pancreas, liver and prostate normal tissues. Stromal (connective tissue) staining was seen in normal breast, colon, duodenum, heart, lung, ovary, prostate, skeletal muscle, skin, stomach and uterus tissues. Normal brain tissue was negative.

TABLE 7

RAAG10 Antibodies binding to Tumor Tissues
Standard Protocol, Abs Concentration = 5 μg/ml

| | Colony number | | | | | | | |
|---|---|---|---|---|---|---|---|---|
| | BLA8 | | SKIN2 | | LUCA1 | | PA20 | |
| Tumor Number | tumor | Stroma | tumor | Stroma | tumor | Stroma | tumor | Stroma |
| Breast | | | | | | | | |
| 6AB3 | ++ | − | + | − | +* | − | +* | − |
| 805A | +/++ | +++ | + | +++ | + | ++ | + | +++ |

TABLE 7-continued

RAAG10 Antibodies binding to Tumor Tissues
Standard Protocol, Abs Concentration = 5 μg/ml

| | BLA8 | | SKIN2 | | LUCA1 | | PA20 | |
|---|---|---|---|---|---|---|---|---|
| Tumor Number | tumor | Stroma | tumor | Stroma | tumor | Stroma | tumor | Stroma |
| Colon | | | | | | | | |
| 1C62 | − | +++ | − | ++ | − | ++ | − | ++ |
| 13FB | + | +++ | − | ++ | + | +++ | + | ++ |
| 27FD | ++ | +++ | + | +++ | − | ++ | − | ++ |
| 4ECD | − | ++ | − | + | − | + | − | − |
| 689F | − | +++ | − | ++ | − | ++ | − | ++ |
| Lung | | | | | | | | |
| 273 | +/++ | +++ | +* | +++ | − | + | − | ++ |
| 34B | ++* | +++ | − | ++ | − | ++ | − | ++ |
| 425 | +* | +++ | − | + | − | ++ | − | ++ |
| E27 | ++ | ++ | ++ | ++ | +/++* | ++ | +* | ++ |
| 380E | +++ | ++ | + | + | +/++ | ++ | + | ++ |
| 1495 | ++ | ++ | + | ++ | +* | ++ | − | ++ |
| Prostate | | | | | | | | |
| 1886 | − | − | − | − | − | − | − | − |
| 209 | +++ | − | ++ | − | ++/+++ | − | ++ | − |
| 470 | ++ | − | ++ | − | ++ | − | + | − |
| 1D2C | +/++ | − | ++ | − | ++ | − | ++/+++ | − |

*= Focal Staining

TABLE 8

Anti-RAAG10 Family Antibodies Binding to Normal Tissues
Standard Protocol (Ab concentration = 5 μg/ml)

| | BLA8 | LUCA1 | PA20 | SKIN2 |
|---|---|---|---|---|
| Skin | | | | |
| Basal epidermis | − | Weak+ | − | Weak+ |
| Vessels | +/− | +/− | +/− | +/− |
| Sweat Glands | − | − | − | − |
| Stroma | +/− | +/− | +/− | +/− |
| Lung | | | | |
| Alveoli | Weak+ | +/− | −/+ | −/+ |
| Bronchial Epithelium | − | − | − | − |
| Liver | | | | |
| Hepatocytes | −/+ | −/+ | −/+ | −/+ |
| Kupffer cells | + | + | + | +/− |
| Vessels | − | − | − | − |
| Pancreas | | | | |
| Acini | −/+ | −/+ | Weak+ | Weak+ |
| Ducts | − | − | − | − |
| Islets | −/+ | −/+ | +/− | +/− |
| Stroma | +/− | +/− | +/− | +/− |
| Kidney | | | | |
| Vessels | − | − | − | − |
| Stroma | +/− | − | − | − |
| Glomeruli | − | +/− | − | − |

Example 14

Internalization of an Anti-RAAG10 Antibody and Toxin-Conjugated Anti-Mouse IgG

MAb-ZAP (Advanced Targeting Systems, San Diego, Calif.) is anti-mouse IgG conjugated to saporin, a toxin that inhibits protein synthesis. This toxin is impermeable to the cell membrane. If a monoclonal antibody is bound to a cell-surface antigen that is internalizable, the toxin-conjugate can bind to the bound monoclonal and be internalized, eventually killing the cell. Being dependent upon internalization for demonstration of toxic activity, the MAb-ZAP can serve to evaluate whether or not a given surface antigen will serve as a suitable target for any toxin that is dependent upon internalization to express cell toxic effects. As such, the MAb-ZAP serves as a model for such internalization-dependent toxins such as maytansinoids and calicheamicins.

For testing the internalization of an anti-RAAG10 antibody and saporin conjugated anti-mouse IgG and the effect of inhibiting tumor cell growth after internalization of the protein synthesis inhibitor saporin, mouse monoclonal anti-RAAG10 antibody LUCA1 was used in the assay. Human lung squamous carcinoma cells, SK-MES-1, were removed from stock flasks with 10 mM EDTA and centrifuged. Cells were resuspended at 50,000/ml in appropriate medium and 100 microl plated per well in 96 well plates. Antibody LUCA1 was added immediately to appropriate wells as a 10× concentrate, to make a final concentration of 10 microg/ml. After 15 minutes at room temperature MAb-ZAP (Cat. #IT-04, Advanced Targeting Systems, San Diego Calif.) was added to appropriate wells as a 10× concentrate, to make final concentrations from 0.001 pM to $10^4$ pM. After 4 days growth, MTT was added (stock 5 mg/ml PBS, 1:10 dilution in well) for 4 hrs at 37° C. The medium was then removed from all wells and 100 microl/well DMSO was added. The plates were gently swirled to solubilize the blue MTT precipitate and the plates were read in a plate reader at 540 nm. The OD measurement of the reduced tetrazolium dye MTT is a surrogate for cell number.

As shown in FIG. 1, there was a decrease in MTT staining in SK-MES-1 cells in the presence (solid line) of LUCA1 monoclonal antibody as compared to the staining in the absence (dotted line) of LUCA1 when MAb-ZAP was added, indicating the growth of human lung squamous carcinoma cells SK-MES-1 was inhibited in the presence of LUCA1 monoclonal antibody and MAb-ZAP (anti-mouse IgG conjugated to the protein synthesis inhibitor saporin). The divergence of the lines at the higher concentrations of MabZAP indicates that LUCA1 is internalized. Similar experiments with LUCA1 have been done on the tumor cell lines SK-OV-3 and LNCaP. Similar internalization results have also been obtained on these three cell lines with BLA8 and KID2 monoclonal antibodies, which are two other anti-RAAG10 antibodies directed to other epitopes than that to which LUCA1 is directed.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

We claim:

1. A method of treating cancer in a subject having a cancer comprising administering to the subject a composition comprising a therapeutically effective amount of an immunoglobulin polypeptide or an antigen-binding fragment thereof associated with a chemotherapeutic agent, wherein:
   said immunoglobulin polypeptide or antigen-binding fragment thereof specifically binds to an epitope of a B7-H3L protein that is expressed and exposed in its native conformation on the surface of a cancer cell of said cancer, wherein said epitope is insufficiently expressed on the surface of a living normal cell to exhibit binding by said immunoglobulin polypeptide;
   said immunoglobulin polypeptide or antigen-binding fragment thereof can be internalized into said cancer cell expressing B7-H3L; and
   said immunoglobulin polypeptide or antigen-binding fragment thereof comprises the amino acid sequences of complementarity determining regions of the monoclonal antibody expressed by the hybridoma having ATCC Deposit No. PTA-4217, ATCC Deposit No. PTA-4218, ATCC Deposit No. PTA-4244, or ATCC Deposit No. PTA-4245.

2. The method of claim 1, wherein said cancer cell is selected from the group consisting of a cancer cell from: an adrenal gland tumor, an AIDS-associated cancer, an alveolar soft part sarcoma, an astrocytic tumor, a bladder cancer, a bone cancer, a brain or spinal cord cancer, a metastatic brain tumor, a breast cancer, a carotid body tumor, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gestational trophoblastic disease, a germ cell tumor, a head and neck cancer, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome cell, a neuroblastoma, a neuroendocrine tumor, an ovarian cancer, a pancreatic cancer, a papillary thyroid carcinoma, a parathyroid tumor, a pediatric cancer cell, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

3. The method of claim 1, wherein said immunoglobulin polypeptide is a monoclonal antibody expressed by the hybridoma having ATCC Deposit No. PTA-4217, ATCC Deposit No. PTA-4218, ATCC Deposit No. PTA-4244, or ATCC Deposit No. PTA-4245.

4. The method of claim 1, wherein said chemotherapeutic agent is delivered into said cancer cell.

5. The method of claim 1, wherein the composition comprises an additional therapeutic moiety.

6. The method of claim 1, further comprising the administration of one or more additional cancer therapies.

7. The method of claim 6, wherein said additional cancer therapy is selected from the group consisting of chemotherapy, radiation therapy, and surgery.

8. The method of claim 1, wherein said administered composition increases antibody-dependent cell mediated cytotoxicity (ADCC).

9. The method of claim 1, wherein said subject is a human.

10. A method for delivering a chemotherapeutic agent to a cancer cell comprising administering to a subject a composition comprising a therapeutically effective amount of an immunoglobulin polypeptide or an antigen-binding fragment thereof associated with the chemotherapeutic agent, wherein:
   said immunoglobulin polypeptide or antigen-binding fragment thereof specifically binds to an epitope of a B7-H3L protein that is expressed and exposed in its native conformation on the surface of the cancer cell, wherein said epitope is insufficiently expressed on the surface of a living normal cell to exhibit binding by said immunoglobulin polypeptide;
   said immunoglobulin polypeptide or antigen-binding fragment thereof can be internalized into said cancer cell expressing B7-H3L; and
   said immunoglobulin polypeptide or antigen-binding fragment thereof comprises the amino acid sequences of complementarity determining regions of the monoclonal antibody expressed by the hybridoma having ATCC Deposit No. PTA-4217, ATCC Deposit No. PTA-4218, ATCC Deposit No. PTA-4244, or ATCC Deposit No. PTA-4245.

11. The method of claim 10, wherein said cancer cell is selected from the group consisting of a cancer cell from: an adrenal gland tumor, an AIDS-associated cancer, an alveolar soft part sarcoma, an astrocytic tumor, a bladder cancer, a bone cancer, a brain or spinal cord cancer, a metastatic brain tumor, a breast cancer, a carotid body tumor, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, a gestational trophoblastic disease, a germ cell tumor, a head and neck cancer, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome cell, a neuroblastoma, a neuroendocrine tumor, an ovarian cancer, a pancreatic cancer, a papillary thyroid carcinoma, a parathyroid tumor, a pediatric cancer cell, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

12. The method of claim 10, wherein said immunoglobulin polypeptide is a monoclonal antibody expressed by the hybridoma having ATCC Deposit No. PTA-4217, ATCC Deposit No. PTA-4218, ATCC Deposit No. PTA-4244, or ATCC Deposit No. PTA-4245.

13. The method of claim 10, wherein said chemotherapeutic agent is delivered into said cancer cell.

14. The method of claim 10, wherein the composition comprises an additional therapeutic moiety.

15. The method of claim 10, wherein said administered composition increases antibody-dependent cell mediated cytotoxicity (ADCC).

16. The method of claim 10, wherein said subject is a human.

* * * * *

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Synthetic construct

<400> SEQUENCE: 1
agccgcctca caggaagatg ct                                             22

<210> SEQ ID NO 2
<211> LENGTH: 24
<212> TYPE: DNA
<213> ORGANISM: Artificial Sequence
<220> FEATURE:
<223> OTHER INFORMATION: Synthetic construct

<400> SEQUENCE: 2
ccctggtcct catggtcagg ctat                                           24

<210> SEQ ID NO 3
<211> LENGTH: 25
<212> TYPE: DNA
<213> ORGANISM: Artificial Sequence
<220> FEATURE:
<223> OTHER INFORMATION: Synthetic construct

<400> SEQUENCE: 3
agcggccacc tgcaggctga cggca                                          25

<210> SEQ ID NO 4
<211> LENGTH: 27
<212> TYPE: DNA
<213> ORGANISM: Artificial Sequence
<220> FEATURE:
<223> OTHER INFORMATION: Synthetic construct

<400> SEQUENCE: 4
ggggaatgtc ataggctgcc ctgtgat                                        27

<210> SEQ ID NO 5
<211> LENGTH: 26
<212> TYPE: DNA
<213> ORGANISM: Artificial Sequence
<220> FEATURE:
<223> OTHER INFORMATION: Synthetic construct

<400> SEQUENCE: 5
ccctactcga agcccagcat gaccct                                         26
```

```
<210> SEQ ID NO 6
<211> LENGTH: 23
<212> TYPE: DNA
<213> ORGANISM: Artificial Sequence
<220> FEATURE:
<223> OTHER INFORMATION: Synthetic construct

<400> SEQUENCE: 6
cacggctcct gtggggcttc tct                                              23

<210> SEQ ID NO 7
<211> LENGTH: 23
<212> TYPE: DNA
<213> ORGANISM: Artificial Sequence
<220> FEATURE:
<223> OTHER INFORMATION: Synthetic construct

<400> SEQUENCE: 7
ccagaggccc tgtgggtgac cgt                                              23

<210> SEQ ID NO 8
<211> LENGTH: 24
<212> TYPE: DNA
<213> ORGANISM: Artificial Sequence
<220> FEATURE:
<223> OTHER INFORMATION: Synthetic construct

<400> SEQUENCE: 8
cagggctcct gtgaggcaga acca                                             24
```